(12) United States Patent
Engelhard et al.

(10) Patent No.: US 10,573,161 B2
(45) Date of Patent: *Feb. 25, 2020

(54) DEVICES, SYSTEMS, AND METHODS FOR ADHERENCE MONITORING AND DEVICES, SYSTEMS, AND METHODS FOR MONITORING USE OF CONSUMABLE DISPENSERS

(71) Applicant: Gecko Health Innovations, Inc., Cambridge, MA (US)

(72) Inventors: Yechiel Engelhard, Boston, MA (US); Mark Maalouf, Cambridge, MA (US)

(73) Assignee: Gecko Health Innovations, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/964,011

(22) Filed: Apr. 26, 2018

(65) Prior Publication Data
US 2018/0247517 A1    Aug. 30, 2018

Related U.S. Application Data

(63) Continuation of application No. 15/656,434, filed on Jul. 21, 2017, now Pat. No. 10,002,517, which is a
(Continued)

(51) Int. Cl.
*G08B 1/08*    (2006.01)
*G08B 21/24*   (2006.01)
(Continued)

(52) U.S. Cl.
CPC ............ *G08B 21/24* (2013.01); *A61J 7/0418* (2015.05); *A61M 15/008* (2014.02);
(Continued)

(58) Field of Classification Search
CPC .............................. G08B 21/24; G08B 24/245
(Continued)

(56) References Cited

U.S. PATENT DOCUMENTS

| 5,042,467 A | 8/1991 | Foley |
| 5,200,891 A | 4/1993 | Kehr et al. |

(Continued)

FOREIGN PATENT DOCUMENTS

| CN | 102159270 A | 8/2011 |
| CN | 202289119 U | 7/2012 |

(Continued)

OTHER PUBLICATIONS

Bateman et al., "Can Guideline-defined Asthma Control Be Achieved?—The Gaining Optimal Asthma ControL Study", American Journal of Respiratory and Critical Care Medicine, vol. 170, No. 8, 2004, pp. 836-844.

(Continued)

*Primary Examiner* — Tai T Nguyen
(74) *Attorney, Agent, or Firm* — Condo Roccia Koptiw LLP

(57) ABSTRACT

Devices, systems, and methods are provided for adherence monitoring, and devices, systems, and methods are provided for monitoring use of consumable dispensers. In general, the devices, systems, and methods can facilitate an individual's adherence to a schedule for consuming consumables and can facilitate monitoring and tracking of the individual's adherence to the schedule. The devices, systems, and methods can allow data regarding the individual's historical adherence to the schedule to be accessible via a computer system. In one embodiment, an accessory is provided that can be configured to attach to consumable dispensers. The accessory can be configured to be removably and replaceably coupled to the dispenser. The accessory can be configured to provide a
(Continued)

notification to a user indicating that a certain event occurred and/or that a certain action needs to be taken. The accessory can be configured to sense attachment thereof to and removal thereof from the dispenser.

18 Claims, 13 Drawing Sheets

Related U.S. Application Data continuation of application No. 14/702,165, filed on May 1, 2015, now Pat. No. 9,728,068, which is a continuation of application No. 14/470,240, filed on Aug. 27, 2014, now Pat. No. 9,035,765.

(60) Provisional application No. 61/871,056, filed on Aug. 28, 2013, provisional application No. 61/871,001, filed on Aug. 28, 2013.

(51) Int. Cl.
*A61M 15/00* (2006.01)
*G06Q 50/22* (2018.01)
*G06F 19/00* (2018.01)
*A61J 7/04* (2006.01)

(52) U.S. Cl.
CPC ....... *A61M 15/009* (2013.01); *G06F 19/3462* (2013.01); *G06Q 50/22* (2013.01); *A61J 7/0436* (2015.05); *A61J 7/0481* (2013.01); *A61J 2200/30* (2013.01); *A61J 2200/70* (2013.01); *A61M 2205/332* (2013.01); *A61M 2205/3331* (2013.01); *A61M 2205/3393* (2013.01); *A61M 2205/3553* (2013.01); *A61M 2205/3576* (2013.01); *A61M 2205/3584* (2013.01); *A61M 2205/3592* (2013.01); *A61M 2205/52* (2013.01); *A61M 2205/581* (2013.01); *A61M 2205/582* (2013.01); *A61M 2205/587* (2013.01); *A61M 2205/8206* (2013.01)

(58) Field of Classification Search
USPC ... 340/539.1, 539.12, 539.32, 505, 540, 541
See application file for complete search history.

(56) References Cited

U.S. PATENT DOCUMENTS

| | | | |
|---|---|---|---|
| 5,284,133 A | 2/1994 | Burns et al. | |
| 5,331,953 A | 7/1994 | Andersson et al. | |
| 5,333,106 A | 7/1994 | Lanpher et al. | |
| 5,338,157 A | 8/1994 | Blomquist | |
| 5,363,842 A | 11/1994 | Mishelevich et al. | |
| 5,505,192 A | 4/1996 | Samiotes et al. | |
| 5,536,249 A | 7/1996 | Castellano et al. | |
| 5,544,647 A | 8/1996 | Jewett et al. | |
| 5,544,661 A | 8/1996 | Davis et al. | |
| 5,602,802 A | 2/1997 | Leigh-Spencer et al. | |
| 5,622,163 A | 4/1997 | Jewett et al. | |
| 5,642,731 A | 7/1997 | Kehr | |
| 5,752,235 A | 5/1998 | Kehr et al. | |
| 5,768,382 A | 6/1998 | Schneier et al. | |
| 5,779,364 A | 7/1998 | Cannelongo et al. | |
| 5,809,997 A | 9/1998 | Wolf | |
| 5,828,751 A | 10/1998 | Walker et al. | |
| 5,839,429 A | 11/1998 | Marnfeldt et al. | |
| 5,842,468 A | 12/1998 | Denyet et al. | |
| 5,887,586 A | 3/1999 | Dahlback et al. | |
| 5,970,143 A | 10/1999 | Schneier et al. | |
| 5,976,082 A | 11/1999 | Wong et al. | |
| 6,018,289 A | 1/2000 | Sekura et al. | |
| 6,039,688 A | 3/2000 | Douglas et al. | |
| 6,084,504 A | 7/2000 | Rosche et al. | |
| 6,102,855 A | 8/2000 | Kehr et al. | |
| 6,148,815 A | 11/2000 | Wolf | |
| 6,168,568 B1 | 1/2001 | Gavriely | |
| 6,190,326 B1 * | 2/2001 | McKinnon | A61B 5/0871 |
| | | | 128/200.24 |
| 6,198,383 B1 | 3/2001 | Sekura et al. | |
| 6,202,642 B1 | 3/2001 | McKinnon et al. | |
| 6,261,238 B1 | 7/2001 | Gavriely | |
| 6,285,731 B1 | 9/2001 | Marnfeldt et al. | |
| 6,375,623 B1 | 4/2002 | Gavriely | |
| 6,383,142 B1 | 5/2002 | Gavriely | |
| 6,390,088 B1 | 5/2002 | Sprenger et al. | |
| 6,424,599 B1 | 7/2002 | Ditzig | |
| 6,540,672 B1 | 4/2003 | Simonsen et al. | |
| 6,561,022 B1 | 5/2003 | Doyle et al. | |
| 6,579,231 B1 | 6/2003 | Phipps | |
| 6,581,357 B1 | 6/2003 | Lindenberger et al. | |
| 6,604,650 B2 | 8/2003 | Sagar | |
| 6,612,985 B2 | 9/2003 | Eiffert et al. | |
| 6,637,430 B1 | 10/2003 | Voges et al. | |
| 6,652,455 B1 | 11/2003 | Kocher | |
| 6,691,058 B2 | 2/2004 | Blakley | |
| 6,697,649 B1 | 2/2004 | Bennett et al. | |
| 6,707,763 B2 | 3/2004 | Osberg et al. | |
| 6,729,327 B2 | 5/2004 | McFarland, Jr. | |
| 6,743,202 B2 | 6/2004 | Hirschman et al. | |
| 6,747,556 B2 | 6/2004 | Medema et al. | |
| 6,751,730 B1 | 6/2004 | Walker et al. | |
| 6,804,558 B2 | 10/2004 | Haller et al. | |
| 6,850,555 B1 | 2/2005 | Barclay | |
| 6,904,907 B2 | 6/2005 | Speldrich et al. | |
| 6,937,150 B2 | 8/2005 | Medema et al. | |
| 6,958,691 B1 | 10/2005 | Anderson et al. | |
| 6,978,780 B1 | 12/2005 | Marnfeldt et al. | |
| 6,990,975 B1 | 1/2006 | Jones et al. | |
| 7,016,744 B2 | 3/2006 | Howard et al. | |
| 7,024,331 B2 | 4/2006 | Jones et al. | |
| 7,072,738 B2 | 7/2006 | Bonney et al. | |
| 7,081,807 B2 | 7/2006 | Lai | |
| 7,133,329 B2 | 11/2006 | Skyggebjerg et al. | |
| 7,138,906 B2 | 11/2006 | Rosche | |
| 7,139,701 B2 | 11/2006 | Harton et al. | |
| 7,151,456 B2 | 12/2006 | Godfrey et al. | |
| 7,170,823 B2 | 1/2007 | Fabricius et al. | |
| 7,191,777 B2 | 3/2007 | Brand et al. | |
| 7,198,172 B2 | 4/2007 | Harvey et al. | |
| 7,201,721 B2 | 4/2007 | Wilkinson | |
| 7,205,775 B2 | 4/2007 | Kreit | |
| 7,228,228 B2 | 6/2007 | Bartlett et al. | |
| 7,233,228 B2 | 6/2007 | Lintell et al. | |
| 7,249,687 B2 | 7/2007 | Anderson et al. | |
| 7,295,890 B2 | 11/2007 | Jean-Pierre | |
| 7,330,101 B2 | 2/2008 | Sekura | |
| 7,343,914 B2 | 3/2008 | Abrams et al. | |
| 7,347,200 B2 * | 3/2008 | Jones | A61M 15/009 |
| | | | 128/200.23 |
| 7,347,824 B2 | 3/2008 | Wilkinson et al. | |
| 7,366,675 B1 | 4/2008 | Walker et al. | |
| 7,383,837 B2 | 6/2008 | Robertson et al. | |
| 7,395,214 B2 | 7/2008 | Shillingburg | |
| 7,397,730 B2 | 7/2008 | Skyggebjerg et al. | |
| 7,424,888 B2 * | 9/2008 | Harvey | A61M 15/0083 |
| | | | 128/203.15 |
| 7,450,974 B2 | 11/2008 | Bennett et al. | |
| 7,454,267 B2 | 11/2008 | Bonney et al. | |
| 7,458,373 B2 | 12/2008 | Nichols et al. | |
| 7,461,655 B2 | 12/2008 | Sexton et al. | |
| 7,481,213 B2 | 1/2009 | Childers | |
| 7,495,546 B2 | 2/2009 | Lintell et al. | |
| 7,515,507 B2 | 4/2009 | Nanda | |
| 7,537,005 B2 | 5/2009 | Dave | |
| 7,553,234 B2 | 6/2009 | Walker et al. | |
| 7,554,434 B1 | 6/2009 | Gifford et al. | |
| 7,639,120 B2 | 12/2009 | Sekura | |
| 7,675,424 B2 | 3/2010 | Debord et al. | |
| 7,680,629 B2 | 3/2010 | Chang et al. | |
| 7,708,697 B2 | 5/2010 | Wilkinson et al. | |
| 7,766,012 B2 | 8/2010 | Scheuch et al. | |
| 7,772,981 B1 | 8/2010 | Lambert et al. | |

(56) References Cited

U.S. PATENT DOCUMENTS

| | | |
|---|---|---|
| 7,796,676 B2 | 9/2010 | Barclay |
| 7,810,745 B2 | 10/2010 | Oomura et al. |
| 7,819,116 B2 | 10/2010 | Brand et al. |
| 7,821,404 B2 | 10/2010 | Walker et al. |
| 7,837,648 B2 | 11/2010 | Blair et al. |
| 7,844,361 B2 | 11/2010 | Jean-Pierre |
| 7,850,618 B2 | 12/2010 | Wilkinson et al. |
| RE42,052 E | 1/2011 | Osborn et al. |
| 7,868,609 B2 | 1/2011 | Zhitomirskiy |
| 7,944,342 B2 | 5/2011 | Sekura |
| 7,945,461 B2 | 5/2011 | Sekura |
| 7,996,106 B2 | 8/2011 | Ervin |
| 8,032,397 B2 | 10/2011 | Lawless |
| 8,055,509 B1 | 11/2011 | Walker et al. |
| 8,066,432 B2 | 11/2011 | Yang et al. |
| 8,069,056 B2 | 11/2011 | Walker et al. |
| 8,091,545 B2 | 1/2012 | Schechter et al. |
| 8,092,224 B2 | 1/2012 | Walker et al. |
| 8,129,985 B2 | 3/2012 | Lee et al. |
| 8,138,939 B2 | 3/2012 | Manning et al. |
| 8,149,111 B2 | 4/2012 | Monroe |
| 8,215,299 B2 | 7/2012 | Wu |
| 8,225,781 B2 | 7/2012 | Ooida et al. |
| 8,231,573 B2 | 7/2012 | Edwards et al. |
| 8,240,301 B2 | 8/2012 | Spaargaren et al. |
| 8,241,223 B2 | 8/2012 | Gavriely et al. |
| 8,262,394 B2 | 9/2012 | Walker et al. |
| 8,269,613 B2 | 9/2012 | Lazar |
| 8,279,076 B2 | 10/2012 | Johnson |
| 8,284,068 B2 | 10/2012 | Johnson |
| 8,286,821 B2 | 10/2012 | Mejia et al. |
| 8,290,792 B2 | 10/2012 | Sekura |
| 8,311,770 B2 | 11/2012 | Yuen et al. |
| 8,319,613 B2 | 11/2012 | Lazar |
| 8,342,172 B2 * | 1/2013 | Levy ............... A61M 15/009 128/200.14 |
| 8,353,752 B2 | 1/2013 | Walker et al. |
| 8,386,042 B2 | 2/2013 | Yudovsky et al. |
| 8,424,517 B2 | 4/2013 | Sutherland et al. |
| 8,446,799 B2 | 5/2013 | Burke et al. |
| 8,448,873 B2 | 5/2013 | Downey et al. |
| 8,456,287 B2 | 6/2013 | Gifford et al. |
| 8,464,707 B2 | 6/2013 | Jongejan et al. |
| 8,485,982 B2 | 7/2013 | Gavish et al. |
| 8,488,505 B2 | 7/2013 | Pyles et al. |
| 8,502,692 B2 | 8/2013 | Johnson |
| 8,517,016 B2 | 8/2013 | Caro et al. |
| 8,528,544 B2 | 9/2013 | Kobayashi |
| 8,534,220 B1 | 9/2013 | Olson |
| 8,538,707 B2 | 9/2013 | Adamo et al. |
| 8,539,945 B2 | 9/2013 | Solomon et al. |
| 8,544,286 B2 | 10/2013 | Janssen |
| 8,547,239 B2 | 10/2013 | Peatfield et al. |
| 8,549,310 B2 | 10/2013 | Walker et al. |
| 8,550,069 B2 | 10/2013 | Alelov |
| 8,560,271 B2 | 10/2013 | Koehler et al. |
| 8,573,203 B2 | 11/2013 | Addington et al. |
| 8,615,413 B2 | 12/2013 | McKee et al. |
| 8,666,539 B2 | 3/2014 | Ervin |
| 8,710,827 B2 | 4/2014 | Zhitomirsky |
| 8,714,150 B2 | 5/2014 | Alelov |
| 8,714,983 B2 | 5/2014 | Kil |
| 8,725,529 B2 | 5/2014 | Hyde et al. |
| 8,727,180 B2 | 5/2014 | Zonana et al. |
| 8,738,395 B2 | 5/2014 | Hyde et al. |
| 8,750,693 B2 | 6/2014 | Sharma et al. |
| 8,754,769 B2 | 6/2014 | Stein et al. |
| 8,771,205 B2 | 7/2014 | Gavriely et al. |
| 8,797,167 B2 | 8/2014 | Bangera et al. |
| 8,807,131 B1 * | 8/2014 | Tunnell ............. A61M 16/0051 128/200.23 |
| 8,823,510 B2 | 9/2014 | Downey et al. |
| 8,830,076 B2 | 9/2014 | Smith et al. |
| 8,838,738 B2 | 9/2014 | Lee et al. |
| 8,844,766 B2 | 9/2014 | Zaima et al. |
| 8,854,225 B2 | 10/2014 | Johnson |
| 8,857,617 B2 | 10/2014 | Balakier et al. |
| 8,869,793 B1 | 10/2014 | Spandorfer et al. |
| 8,896,428 B2 | 11/2014 | Shalala |
| 8,909,487 B2 | 12/2014 | Adamo et al. |
| 8,922,367 B2 | 12/2014 | Denny et al. |
| 8,960,189 B2 | 2/2015 | Morrison et al. |
| 8,976,036 B2 | 3/2015 | Johnson |
| 8,997,735 B2 | 4/2015 | Zierenberg et al. |
| 9,007,875 B2 | 4/2015 | Nurse et al. |
| 9,014,427 B2 | 4/2015 | Bear et al. |
| 9,027,795 B2 | 5/2015 | Zaima et al. |
| 9,046,403 B2 | 6/2015 | Ortenzi et al. |
| 9,056,174 B2 | 6/2015 | Bradshaw et al. |
| 9,058,410 B2 | 6/2015 | McKee et al. |
| 9,072,654 B2 | 7/2015 | Pentz |
| 9,081,885 B2 | 7/2015 | Bangera et al. |
| 9,084,566 B2 | 7/2015 | Zdeblick |
| 9,125,798 B2 | 9/2015 | Stein et al. |
| 9,145,000 B2 | 9/2015 | Lakin et al. |
| 9,168,343 B2 | 10/2015 | Scarrott et al. |
| 9,174,009 B2 | 11/2015 | Peatfield et al. |
| 9,188,579 B2 | 11/2015 | Shen et al. |
| 9,216,267 B2 | 12/2015 | Spandorfer et al. |
| 9,235,689 B2 | 1/2016 | Ervin |
| 9,235,690 B2 | 1/2016 | Bear et al. |
| 9,242,056 B2 | 1/2016 | Andersen et al. |
| 9,272,531 B2 | 3/2016 | Lakin et al. |
| 9,278,177 B2 | 3/2016 | Edwards et al. |
| 9,283,027 B2 | 3/2016 | Monson et al. |
| 9,295,793 B2 | 3/2016 | Ferris et al. |
| 9,308,151 B2 | 4/2016 | Chaturvedi et al. |
| 9,308,334 B2 | 4/2016 | Dudley et al. |
| 9,311,452 B2 | 4/2016 | Dickie et al. |
| 9,314,292 B2 | 4/2016 | Trees et al. |
| 9,317,663 B2 | 4/2016 | Dickie et al. |
| 9,339,188 B2 | 5/2016 | Proud |
| 9,339,616 B2 | 5/2016 | Denny et al. |
| 9,352,107 B2 | 5/2016 | Von Hollen et al. |
| 9,358,183 B2 | 6/2016 | Stein et al. |
| 9,361,431 B2 | 6/2016 | Fauci |
| 9,361,772 B2 | 6/2016 | Johnson |
| 9,361,780 B2 | 6/2016 | Burke et al. |
| 9,364,619 B2 | 6/2016 | Overfield et al. |
| 9,392,939 B2 | 7/2016 | Proud |
| 9,398,854 B2 | 7/2016 | Proud |
| 9,427,534 B2 | 8/2016 | Bruin et al. |
| 9,460,265 B2 | 10/2016 | Burrows et al. |
| 9,463,291 B2 | 10/2016 | Imran et al. |
| 9,468,729 B2 | 10/2016 | Sutherland et al. |
| 9,501,626 B2 | 11/2016 | Zhang et al. |
| 9,542,826 B2 | 1/2017 | Edwards et al. |
| 9,550,031 B2 | 1/2017 | Van Sickle et al. |
| 9,694,147 B2 | 7/2017 | Peatfield et al. |
| 9,736,642 B2 | 8/2017 | Ostrander et al. |
| 9,839,398 B2 | 12/2017 | Yamamori et al. |
| 9,911,308 B2 | 3/2018 | Edwards et al. |
| 9,956,360 B2 | 5/2018 | Germinario et al. |
| 9,962,507 B2 | 5/2018 | Germinario et al. |
| 9,962,508 B2 | 5/2018 | Bruin et al. |
| 10,016,134 B2 | 7/2018 | Hansen et al. |
| 10,046,121 B2 | 8/2018 | Kolb et al. |
| 10,155,094 B2 | 12/2018 | Wachtel et al. |
| 2002/0073196 A1 | 6/2002 | Westervelt et al. |
| 2002/0185128 A1 | 12/2002 | Theobald et al. |
| 2003/0052135 A1 | 3/2003 | Conley |
| 2003/0098022 A1 | 5/2003 | Nakao et al. |
| 2003/0099158 A1 | 5/2003 | De la Huerga |
| 2003/0192535 A1 | 10/2003 | Christrup et al. |
| 2003/0234198 A1 | 12/2003 | Weinstein et al. |
| 2004/0089299 A1 | 5/2004 | Bonney et al. |
| 2004/0117062 A1 | 6/2004 | Bonney et al. |
| 2004/0148199 A1 | 7/2004 | Dixon, Jr. |
| 2004/0199056 A1 | 10/2004 | Husemann et al. |
| 2005/0021286 A1 | 1/2005 | Kunce |
| 2005/0028815 A1 | 2/2005 | Deaton et al. |
| 2005/0086256 A1 | 4/2005 | Owens et al. |
| 2005/0119604 A1 | 6/2005 | Bonney et al. |
| 2005/0150488 A1 | 7/2005 | Dave |

(56) References Cited

U.S. PATENT DOCUMENTS

| | | |
|---|---|---|
| 2005/0161467 A1 | 7/2005 | Jones et al. |
| 2005/0172958 A1 | 8/2005 | Singer et al. |
| 2005/0174216 A1 | 8/2005 | Lintell |
| 2005/0247312 A1 | 11/2005 | Davies et al. |
| 2005/0251289 A1 | 11/2005 | Bonney et al. |
| 2006/0089545 A1 | 4/2006 | Ratjen et al. |
| 2006/0231109 A1 | 10/2006 | Howell et al. |
| 2006/0237001 A1 | 10/2006 | Stangl et al. |
| 2006/0237002 A1 | 10/2006 | Bonney et al. |
| 2006/0241510 A1 | 10/2006 | Halperin et al. |
| 2007/0023034 A1 | 2/2007 | Jongejan et al. |
| 2007/0118054 A1 | 5/2007 | Pinhas et al. |
| 2007/0186923 A1 | 8/2007 | Poutiatine et al. |
| 2007/0271298 A1 | 11/2007 | Juang et al. |
| 2008/0119958 A1 | 5/2008 | Bear et al. |
| 2008/0125724 A1 | 5/2008 | Monroe |
| 2008/0147211 A1 | 6/2008 | Teller |
| 2008/0173301 A1 | 7/2008 | Deaton et al. |
| 2008/0178872 A1 | 7/2008 | Genova et al. |
| 2008/0201169 A1 | 8/2008 | Galasso et al. |
| 2008/0230057 A1 | 9/2008 | Sutherland et al. |
| 2008/0246599 A1 | 10/2008 | Hufton et al. |
| 2008/0269625 A1 | 10/2008 | Halperin et al. |
| 2008/0281636 A1 | 11/2008 | Jung et al. |
| 2009/0128330 A1 | 5/2009 | Monroe |
| 2009/0194104 A1 | 8/2009 | Van Sickle |
| 2009/0221308 A1 | 9/2009 | Lerner et al. |
| 2009/0308387 A1 | 12/2009 | Andersen et al. |
| 2009/0314292 A1 | 12/2009 | Overfield et al. |
| 2009/0326861 A1 | 12/2009 | Langford et al. |
| 2010/0078022 A1 | 4/2010 | Striebig et al. |
| 2010/0164716 A1 | 7/2010 | Estevez et al. |
| 2010/0192948 A1 | 8/2010 | Sutherland et al. |
| 2010/0242960 A1 | 9/2010 | Zangerle et al. |
| 2010/0250280 A1 | 9/2010 | Sutherland et al. |
| 2010/0252036 A1 | 10/2010 | Sutherland et al. |
| 2011/0180563 A1 | 7/2011 | Fitchett et al. |
| 2011/0253139 A1 | 10/2011 | Guthrie et al. |
| 2011/0282693 A1 | 11/2011 | Craft et al. |
| 2012/0012106 A1 | 1/2012 | Bari |
| 2012/0123842 A1 | 5/2012 | Patel et al. |
| 2012/0173319 A1 | 7/2012 | Ferrara |
| 2012/0218106 A1 | 8/2012 | Zaima et al. |
| 2012/0232983 A1 | 9/2012 | Bertha et al. |
| 2012/0245960 A1 | 9/2012 | Bartholomew et al. |
| 2013/0096843 A1 | 4/2013 | Yuen et al. |
| 2013/0137998 A1 | 5/2013 | Lange et al. |
| 2013/0144178 A1 | 6/2013 | Halperin et al. |
| 2013/0151196 A1 | 6/2013 | Yuen et al. |
| 2013/0197445 A1 | 8/2013 | Schabbach et al. |
| 2013/0200097 A1 | 8/2013 | Yang et al. |
| 2013/0245502 A1 | 9/2013 | Lange et al. |
| 2013/0269685 A1 | 10/2013 | Wachtel et al. |
| 2013/0269694 A1 | 10/2013 | Patton et al. |
| 2013/0304502 A1 | 11/2013 | Cederlund et al. |
| 2013/0325396 A1 | 12/2013 | Yuen et al. |
| 2013/0325399 A1 | 12/2013 | Yuen et al. |
| 2013/0325404 A1 | 12/2013 | Yuen et al. |
| 2013/0334248 A1 | 12/2013 | Iseri et al. |
| 2014/0000598 A1* | 1/2014 | Sutherland ........ A61M 15/0065 128/203.12 |
| 2014/0012099 A1 | 1/2014 | Halperin et al. |
| 2014/0039839 A1 | 2/2014 | Yuen et al. |
| 2014/0039840 A1 | 2/2014 | Yuen et al. |
| 2014/0039841 A1 | 2/2014 | Yuen et al. |
| 2014/0039842 A1 | 2/2014 | Yuen et al. |
| 2014/0052790 A1 | 2/2014 | Yuen et al. |
| 2014/0065219 A1 | 3/2014 | Bosch et al. |
| 2014/0106324 A1 | 4/2014 | Adams et al. |
| 2014/0155841 A1 | 6/2014 | Dossin |
| 2014/0182584 A1* | 7/2014 | Sutherland .......... A61M 15/009 128/200.23 |
| 2014/0207204 A1 | 7/2014 | Halperin et al. |
| 2014/0213925 A1 | 7/2014 | Chan et al. |
| 2014/0262918 A1 | 9/2014 | Chu |
| 2014/0263426 A1 | 9/2014 | Gasper |
| 2014/0266575 A1 | 9/2014 | Pelfrey |
| 2015/0193597 A1 | 7/2015 | Cederlund |
| 2015/0283341 A1 | 10/2015 | Adams et al. |
| 2015/0290396 A1 | 10/2015 | Nagar et al. |
| 2016/0042154 A1 | 2/2016 | Goldberg et al. |
| 2016/0082208 A1 | 3/2016 | Ballam et al. |
| 2016/0103966 A1 | 4/2016 | Mirza |
| 2016/0128389 A1 | 5/2016 | Lamb et al. |
| 2016/0166766 A1 | 6/2016 | Schuster et al. |
| 2016/0228657 A1 | 8/2016 | Sutherland et al. |
| 2016/0256639 A1 | 9/2016 | Van Sickle et al. |
| 2016/0314256 A1 | 10/2016 | Su et al. |
| 2017/0079557 A1 | 3/2017 | Lauk et al. |
| 2017/0109493 A1 | 4/2017 | Hogg et al. |
| 2017/0140125 A1 | 5/2017 | Hogg et al. |
| 2017/0164892 A1 | 6/2017 | Sezan et al. |
| 2017/0173279 A1 | 6/2017 | Sutherland et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg et al. |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0052964 A1 | 2/2018 | Adelson et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |

FOREIGN PATENT DOCUMENTS

| | | |
|---|---|---|
| CN | 102695535 A | 9/2012 |
| CN | 204864412 U | 12/2015 |
| CN | 205073444 U | 3/2016 |
| CN | 205073448 U | 3/2016 |
| EP | 1135056 B1 | 8/2006 |
| EP | 1688746 A2 | 8/2006 |
| EP | 1736133 A2 | 12/2006 |
| EP | 1970087 A2 | 9/2008 |
| EP | 1992381 A1 | 11/2008 |
| EP | 1423046 B1 | 1/2010 |
| EP | 2186471 A1 | 5/2010 |
| EP | 2384782 A1 | 11/2011 |
| EP | 3228345 A1 | 10/2017 |
| FR | 2987997 A1 | 9/2013 |
| JP | 2003-510736 A | 3/2003 |
| JP | 2011-092418 A | 5/2011 |
| WO | WO/1995/022365 A1 | 8/1995 |
| WO | WO 1998/038909 A1 | 9/1998 |
| WO | WO 1999/053982 A1 | 10/1999 |
| WO | WO/1999/063901 A1 | 12/1999 |
| WO | WO 2000/002779 A1 | 1/2000 |
| WO | WO 2000/032088 A1 | 6/2000 |
| WO | WO 2001/024690 A2 | 4/2001 |
| WO | WO 2001/026020 A1 | 4/2001 |
| WO | WO 2002/000280 A2 | 1/2002 |
| WO | WO 2002/053022 A2 | 7/2002 |
| WO | WO/2003/063754 A1 | 8/2003 |
| WO | WO 2003/073977 A2 | 9/2003 |
| WO | WO 2004/084116 A1 | 9/2004 |
| WO | WO 2005/028008 A1 | 3/2005 |
| WO | WO 2006/068623 A1 | 6/2006 |
| WO | WO/2017/051389 A1 | 3/2007 |
| WO | WO/2009/003989 A1 | 1/2009 |
| WO | WO2011/083377 A1 | 12/2010 |
| WO | WO 2011/135353 A1 | 11/2011 |
| WO | WO 2012/095829 A2 | 7/2012 |
| WO | WO 2012/110700 A1 | 8/2012 |
| WO | WO 2013/126897 A1 | 8/2013 |
| WO | WO 2014/004437 A1 | 1/2014 |
| WO | WO 2014-064691 A2 | 5/2014 |
| WO | WO 2015/002492 A1 | 1/2015 |
| WO | WO/2016/043601 A1 | 3/2016 |
| WO | WO/2017/005605 A1 | 1/2017 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO/2017/180980 A1 | 10/2017 |

(56) References Cited

FOREIGN PATENT DOCUMENTS

| WO | WO/2017/189712 A1 | 11/2017 |
| WO | WO/2018/128976 A1 | 7/2018 |
| WO | WO/2018/134552 A1 | 7/2018 |
| WO | WO/2018/134553 A1 | 7/2018 |

OTHER PUBLICATIONS

Doser, "Doser™ Product Description", Available at https://www.doser.com/dWhat.html, retrieved on Jun. 22, 2017, 1999, 2 pages.

Frey et al., "Complexity of Chronic Asthma and Chronic Obstructive Pulmonary Disease: Implications for Risk Assessment, and Disease Progression and Control", Lancet, vol. 372, No. 9643, Sep. 20, 2008, pp. 1088-1099.

Isonea, "Technology", Available at https://web.archive.org/web/20131012033714/http:/isoneamed.com/products/productstechnology , 2011.

Miller, R. R., "Attacking Asthma with Advanced Telehealth Monitoring", AT&T, Dec. 17, 2012, 3 pages.

Moorman et al., "National Surveillance for Asthma", Morbidity and Mortality Weekly Report, Surveillance Summaries, vol. 56, No. SS-8, Oct. 19, 2007, 57 pages.

Nathan et al., "Development of the Asthma Control Test: A Survey for Assessing Asthma Control", The Journal of Allergy and Clinical Immunology, vol. 113, No. 1, Jan. 2004, pp. 59-65.

National Heart, Lung, and Blood Institute, "Expert Panel Report 3: Guidelines for the Diagnosis and Management of Asthma", National Asthma Education and Prevention Program, 2007, pp. 1-440.

Nike, "Nike+ Fuelband", Available at https://web.archive.org/web/201306020727/http://www.nike.com/us/en_us/lp/nikeplusfuelband , 2012.

Propeller Health, "How It Works", Available at http://propellerhealth.com/solutions/ , 2013, 5 pages.

Propeller Health, "Patients", Available at http://propellerhealth.com/solutions/patients, 2013, 5 pages.

Propeller Health, "Payers", Available at http://propellerhealth.com/solutions/payers , 2013, 5 pages.

Propeller Health, "Providers", Available at http://propellerhealth.com/solutions/providers , 2013, 5 pages.

Smartinhaler, "Smartinhaler Tracker", Available at https://web.archive.org/web/20130125222221/http:/www.smartinhaler.com/clinical/products/smartinhalertracker.aspx , 2011, 1 page.

\* cited by examiner

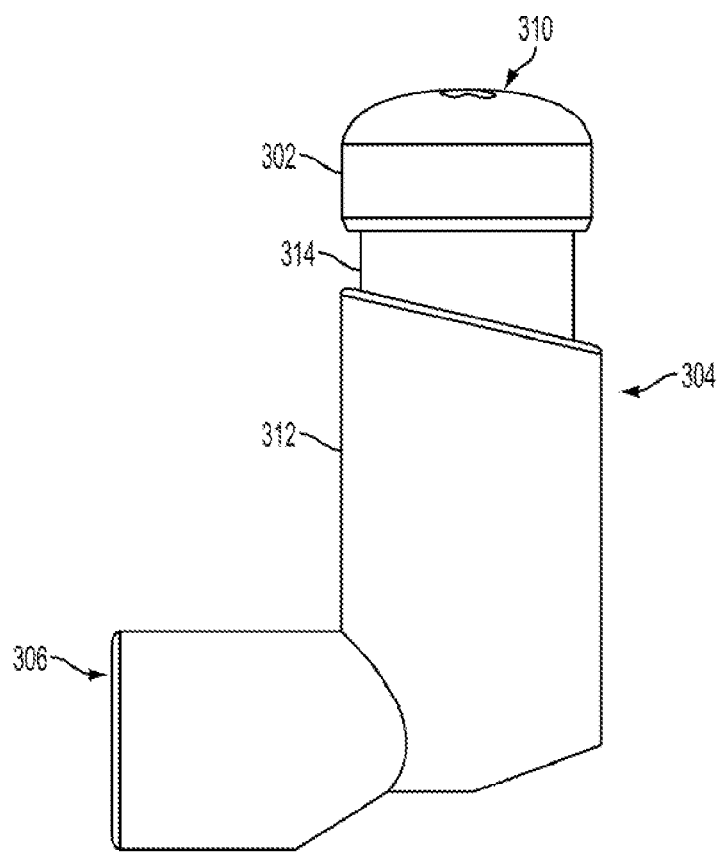
FIG. 4
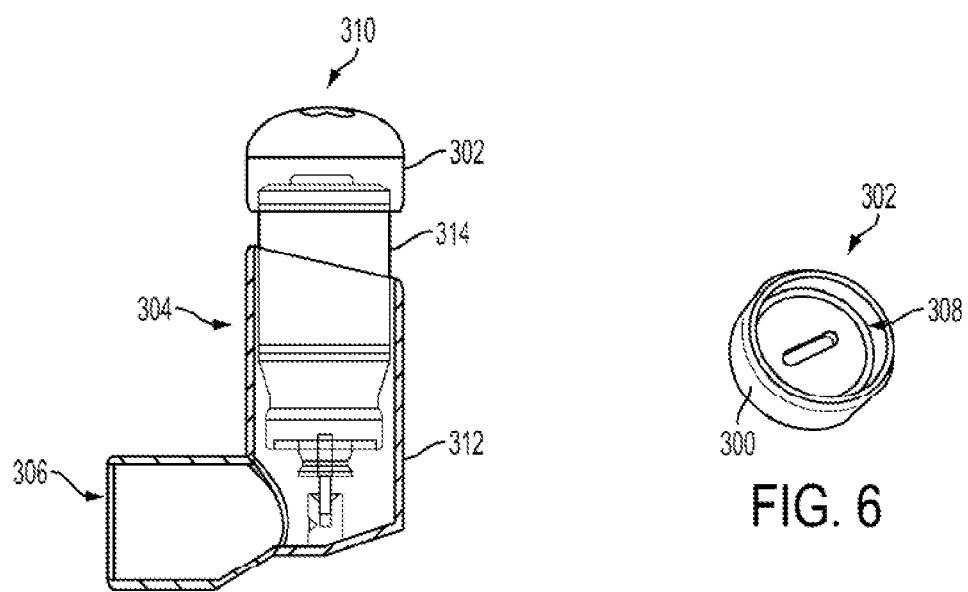
FIG. 5
FIG. 6

DEVICES, SYSTEMS, AND METHODS FOR ADHERENCE MONITORING AND DEVICES, SYSTEMS, AND METHODS FOR MONITORING USE OF CONSUMABLE DISPENSERS

CROSS REFERENCE TO RELATED APPLICATIONS

This application is a continuation to U.S. Patent application Ser. No. 15/656,434 filed Jul. 21, 2017, now issued as U.S. Pat. No. 10,002,517 on Jun. 19, 2018; which is a continuation to U.S. patent Ser. No. 14/702,165 filed May 1, 2015, now issued as U.S. Pat. No. 9,728,068 on Aug. 8, 2017; which is a continuation to U.S. patent application Ser. No. 14/470,240 filed on Aug. 27, 2014, now issued as U.S. Pat. No. 9,035,765 on May 19, 2015; which claims priority to U.S. Provisional Patent Application No. 61/871,001 filed on Aug. 28, 2013, and to U.S. Provisional Patent Application No. 61/871,056 filed on Aug. 28, 2013, the contents of which are hereby incorporated by reference herein.

FIELD OF THE INVENTION

The present invention relates generally to devices, systems, and methods for adherence monitoring and devices, systems, and methods for monitoring use of consumable dispensers.

BACKGROUND OF THE INVENTION

Consumables such as medication, vitamins, and supplements can effectively benefit an individual's health. Consumables are typically consumed on a regular, usually daily, schedule. The closer a patient adheres to the schedule, the better the patient's condition can be managed, e.g., because adequate amounts of the consumable can be consistently present in the patient's system to consistently control adverse effects of a health condition such as asthma. Consumables for respiratory conditions, for dermatological issues, for cardiac issues, etc., can be prescribed for dosage on a regular schedule and can have their maximized effectiveness if taken on the regular schedule.

It can be difficult for patients to adhere to their treatment schedule for a variety of reasons, such as unfamiliarity with a new treatment schedule, being busy with an activity such as work, school, napping, or athletics, and simply forgetting to take the consumables on schedule. It can be particularly difficult for children to remember to take their consumables on schedule, particularly if any doses are required while a child is away from their parent or guardian, such as during school or while at summer camp. Non-adherence to a prescribed schedule can cause any number of adverse effects, such as unnecessary exacerbations, repeating symptoms, required doses of emergency treatment medication, and/or hospital emergency room visits. Adhering to a schedule can thus help better maintain a patient's health, help reduce instances of emergency medication administration, and/or help reduce health care costs by requiring fewer emergency hospital visits or other medical practitioner consultations.

Accordingly, there remains a need for improved devices, systems, and methods for adherence monitoring and devices, systems, and methods for monitoring use of consumable dispensers.

SUMMARY OF THE INVENTION

In one embodiment, an apparatus is provided that includes a mechanical accessory removably and replaceably attachable to a consumables container that is movably coupled to a housing such that the movement of the container and the accessory as a unit relative to the housing is effective to dispense the consumable. The accessory can include a sensor configured to sense when the accessory is attached to the container, a processor, and a wireless communication mechanism. The processor can be configured to cause the wireless communication mechanism to wirelessly transmit data indicative of the sensed attachment to an external device that is external to the accessory and the dispenser. The accessory can be configured to determine when the consumable is dispensed from the container.

The apparatus can vary in any number of ways. For example, the sensor can be configured to sense when the accessory is removed from the container, and the processor can be configured to receive a second signal from the sensor in response to the sensor sensing the accessory being removed from the container. For another example, the sensor can include at least one of a motion sensor and a pressure sensor, and the sensor can be configured to sense when the consumable is dispensed from the dispenser. For yet another example, the sensor can be configured to sense when an electrical circuit is closed, thereby indicating that the accessory has been attached to the container. For another example, the apparatus can include a memory. The sensor can be configured to trigger the processor to store data in the memory regarding the attachment in response to the sensor sensing the attachment, and the data transmitted by the wireless communication mechanism can include the stored data.

In some embodiments, the sensor can include a pressure sensor. The pressure sensor can be configured to have pressure applied thereto by the container in response to the accessory being attached to the container. The processor can be configured to determine that the accessory has been attached to the container when the pressure sensor has the pressure applied thereto. The pressure sensor can be configured to have the pressure released therefrom in response to the accessory being removed from the container, and the processor can be configured to determine that the accessory has been removed from the container when the pressure sensor has the pressure released therefrom.

In some embodiments, the sensor can include a motion sensor. The processor can be configured to determine that the accessory has been attached to the dispenser when the motion sensor senses a first predetermined motion of the accessory. The processor can be configured to determine that the accessory has been removed from the dispenser when the motion sensor senses a second predetermined motion of the accessory that is different from the first predetermined motion.

In some embodiments, the apparatus can include a second sensor configured to sense when the consumable is dispensed from the container. The apparatus can include a second mechanical accessory attachable to the dispenser. The second accessory can include the second sensor. The accessory can include the sensor at a first location and can include the second sensor at a location that is different from the first location.

In another embodiment, an apparatus is provided that includes a mechanical accessory removably and replaceably attachable to a consumables dispenser containing a consumable that is dispensable from the dispenser. The accessory can include a sensor configured to sense attachment of the accessory to the dispenser using one of pressure sensing and motion sensing, a processor configured to cause the accessory to provide a first notification in response to the sensor sensing that the accessory is attached to the dispenser so as to notify a user that the accessory has been attached to the dispenser, and a wireless communication mechanism. The processor can be configured to cause the wireless communication mechanism to wirelessly transmit data to an external device that is external to the accessory and the dispenser. The accessory can be configured to determine when the consumable is dispensed from the dispenser.

The apparatus can have any number of variations. For example, the sensor can include at least one of a motion sensor and a pressure sensor, and the sensor can be configured to sense when the consumable is dispensed from the dispenser. For another example, the sensor can be configured to sense when the accessory is removed from the dispenser, and the processor can be configured to provide a second notification when the sensor senses that the accessory is removed from the dispenser so as to notify the user that the accessory has been removed from the dispenser. For yet another example, the apparatus can include a second sensor configured to sense when the consumable is dispensed from the dispenser. For another example, the dispenser can include a housing having the consumable disposed therein, the accessory can be removably and replaceably attachable to an external surface of the housing, and the housing can include at least one of a pill bottle, a pill box, a squeezable tube, a squeezable bottle, a syringe, a blister pack, and a respiratory inhaler.

In some embodiments, the apparatus can include a housing and a container. The container can be disposed within the housing, the container can contain the consumable therein, and the container can be movable relative to the housing so as to cause the consumable to be dispensed. The accessory can be removably and replaceably attachable to the container such that the accessory is movable with the container relative to the housing so as to cause the consumable to be dispensed.

In another aspect, a method is provided that in one embodiment includes attaching a mechanical accessory to a container of a consumables dispenser movably disposed within a housing of the consumables dispenser, and moving the accessory and the container relative to the housing so as to dispense a consumable contained in the container. A sensor can sense the attachment, and a transmitter can wirelessly transmit first data from the accessory to an external device. The first data can be indicative of the sensed attachment. The external device can be external to the accessory and the dispenser. The transmitter can wirelessly transmit second data from the accessory to the external device. The second data can be indicative of the dispensing.

The method can vary in any number of ways. For example, the method can include detaching the accessory from the container. The sensor can sense the detachment, the transmitter can wirelessly transmit third data from the accessory to the external device, and the third data can be indicative of the sensed detachment. For another example, the method can include, after the sensed detachment, attaching the accessory to a second container containing a second consumable. The sensor can sense the attachment of the accessory to the second container, the transmitter can wirelessly transmit third data from the accessory to the external device, and the third data can be indicative of the sensed attachment to the second container. For yet another example, the method can include, with the accessory attached to the dispenser, providing a notification to a user indicating that the consumable is due to be consumed according to a predetermined schedule.

BRIEF DESCRIPTION OF THE DRAWINGS

The invention will be more fully understood from the following detailed description taken in conjunction with the accompanying drawings, in which:

FIG. 4 is a side view of one embodiment of a consumables dispenser having an accessory removably and replaceably attached thereto;

FIG. 5 is a side partially transparent view of the consumables dispenser and the accessory of FIG. 4;

FIG. 6 is a perspective view of the accessory of FIG. 4;

DETAILED DESCRIPTION OF THE INVENTION

Figure 1:
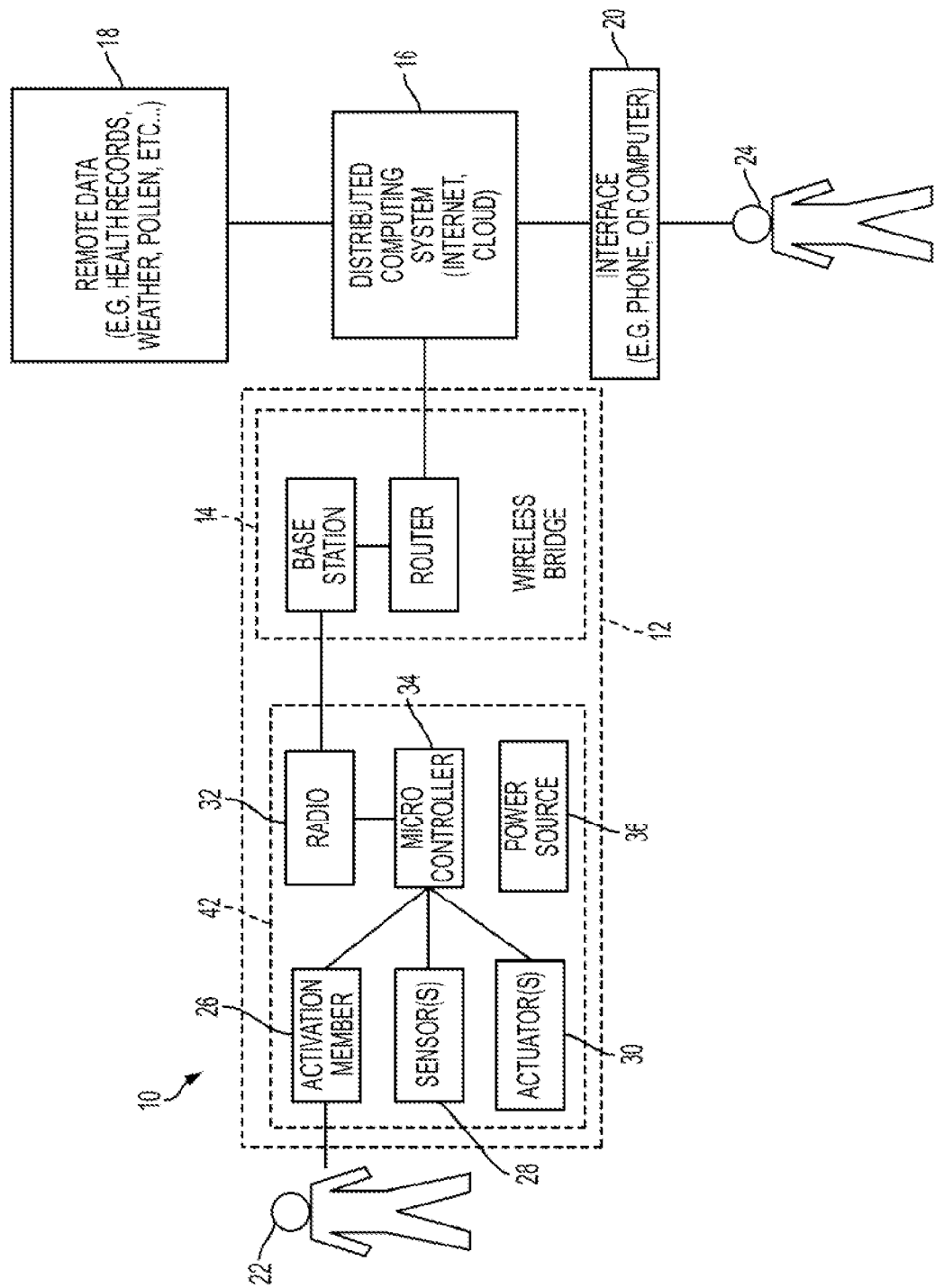
FIG. 1 is a schematic view of one embodiment of a consumables administration, management, and review system.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will appreciate that an equivalent to such linear and circular dimensions can be easily determined for any geometric shape.

Various exemplary devices, systems, and methods are provided for adherence monitoring and devices, systems, and methods for monitoring use of consumable dispensers. In general, the devices, systems, and methods can facilitate an individual's adherence to a schedule for consuming consumables and can facilitate monitoring and tracking of the individual's adherence to the schedule. The devices, systems, and methods can allow data regarding the individual's historical adherence to the schedule to be accessible via a computer system. A user such as the individual, the individual's family, the individual's care provider, a director of a clinical trial involving the individual, etc. can thus access the adherence data even when remotely located from the individual, which can facilitate evaluation and/or modification of the individual's treatment involving the consumable, facilitate evaluation and/or modification of the clinical trial involving the individual, and/or can facilitate incentivizing the individual to adhere to the schedule. Examples of consumables include medications, vitamins, supplements, foods, and cosmetics.

In one embodiment, an accessory is provided that can be configured to attach to consumable dispensers, e.g., pill bottles, asthma inhalers, etc. The consumable dispensers can be existing dispensers retrofitted with the accessory or can be custom-made dispensers integrated with the accessory. The accessory can include a notification mechanism configured to provide a notification to a user indicating that a certain event occurred and/or that a certain action needs to be taken. For example, the accessory can include a light source (e.g., a light emitting diode (LED)) configured to light up when the next dose (also referred to herein as a "dosage") of a consumable is due, a speaker configured to provide an audible sound when the next dose of a consumable is due, a vibration mechanism configured to vibrate when the next dose of a consumable is due, and/or a temperature-changing element configured to increase or decrease in temperature when the next dose of a consumable is due. The accessory can include an on-board timer configured to trigger the notification mechanism to provide a notification, e.g., light, sound, vibration, etc. The accessory can also include a power source, e.g., a battery, configured to power the timer and the notification mechanism. The notification can help people of any age more easily adhere to their consumables schedule. Ailments such as asthma can therefore be better regulated through maintenance treatment, and people can be less likely to need to resort to unscheduled, emergency treatments, such as use of a rescue inhaler. The accessory can be configured to detect usage of the dispenser by being pressed when a consumable is dispensed from the dispenser so as to "wake up" a processor coupled to the accessory. In response to the detected usage, the processor can be configured to record the date and time of the dispenser's usage in a storage unit, such as an on-board memory. The stored data can be transmitted to an external source, e.g., computer system, that can store the data in a network cloud, where the data can be accessed via a user interface, such as a web interface. The user interface can allow a user to view and/or analyze the person's consumable usage trends.

In an exemplary embodiment, the accessory can be configured to be removably and replaceably coupled to the dispenser. The accessory can be configured to be used in any adherence/compliance application for consumables, such as creams for dermatology patients, inhalers for non-asthma respiratory ailments, pill bottles, blister packs, pill boxes, syringes, squeezable bottles, and squeezable tubes. The accessory can thus be configured for use in monitoring and improving adherence and compliance for people and care-providers of people (e.g., doctors, parents, etc.) who could benefit from improved adherence, environmental monitoring, and/or behavior modification. For example, it can be beneficial for certain consumables to be consumed at a same time every day. The accessory can be configured to monitor use of a dispenser that dispenses consumables, thereby facilitating a person's adherence to a schedule of consuming the consumable at a same time every day and/or monitoring the person's adherence to the schedule.

The accessory can be configured to detect attachment and detachment thereof from a consumables dispenser. The detection of the attachment can facilitate registration of the accessory when attached to the dispenser, e.g., registration of the accessory over a network to facilitate association of the accessory with a specific person, a specific consumable, and/or a specific dispenser. The detection of the removal can facilitate various actions regarding the accessory and/or the consumable associated with the consumables dispenser from which the accessory has been removed. For example, the detection of the removal can facilitate timely reattachment of the accessory to the dispenser if the accessory was accidentally removed therefrom. For another example, detection of the removal can signal to a care provider of a person that the person's accessory was removed from the person's consumable dispenser, thereby indicating that the person may be less likely to consume the consumable according to a predetermined schedule and/or that the care provider should discuss the reason for the accessory's removal with the person.

FIG. 1 illustrates one exemplary embodiment of a system 10 configured to facilitate adherence monitoring and monitoring use of consumable dispensers. The system 10 can include a mechanical accessory 12 (also referred to herein as an "accessory"), a wireless bridge 14, a network 16 (also referred to herein as a "distributed computing system"), a memory 18, and an interface 20 (also referred to herein as a "computer system" and a "client station"). In general, the accessory 12 can be attached to a consumables dispenser (not shown) configured to dispense a consumable disposed therein. The dispenser can include any of a variety of dispensers, such as an asthma inhaler, an inhaler for a non-asthma respiratory ailment, a liquid or semi-liquid dispenser such as a medicament tube or pump such as for a topical cream or a topical gel, blister packs for capsules and/or other types of pills, a pill bottle, a syringe, a squeezable bottle, and a squeezable tube. The accessory 12 can be configured to detect attachment of the accessory to the dispenser, detect removal of the accessory from the dispenser, detect usage of the dispenser so as to determine when a consumable has been dispensed from the dispenser, and/or provide a notification to a person 22 when a consumable from the dispenser is due according to a predetermined schedule.

The accessory 12 can be configured to provide data regarding dispensing of the consumable to an external device, such as the interface 20. The data can be transmitted from the accessory 12 to the interface 20 using wireless communication, e.g., Bluetooth, WiFi, etc., over the network 16, e.g., the Internet, a cloud, a local area network (LAN), etc., via the wireless bridge 14. However, as will be appreciated by a person skilled in the art, the system 10 need not include the wireless bridge 14 if the accessory 12 is configured to communicate over the network 16 using a wired connection instead of a wireless connection. The data communicated to the interface 20 from the accessory 12 can optionally be supplemented with data stored in and transmitted from the memory 18, such as health record data for the person 22 (e.g., complete electronic health record (EHR) of the person 22, person name, person age, person medical record number, any medications or other consumables being taken by the person 22, identities of care providers for the person 22, medical diagnoses of the person 22, data for the person 22 previously transmitted by the accessory 12, geographic home of the person 22, etc.) and environmental data (which can be helpful in analyzing data for asthma and other respiratory ailments) such as weather data, traffic data, dust data, and pollen data. Similarly, data transmitted to the memory 18 can be stored therein so as to be associated with a record already stored therein, e.g., data gathered by the accessory 12 being added to the person's EHR stored in the memory 18. The interface 20 can be configured to analyze the data received from the accessory 12 and can be configured to provide the received data and/or results of the analysis on a user interface (not shown) for review by one or more users such as the person 22 and a user 24 associated with the person 22, such as a family member of the person 22, a friend of the person 22, or a medical care provider (doctor, nurse, clinical trial director, etc.) for the person 22. In an exemplary embodiment, the user interface can be customized based on an identity of the user accessing the interface 20.

Figure 2:
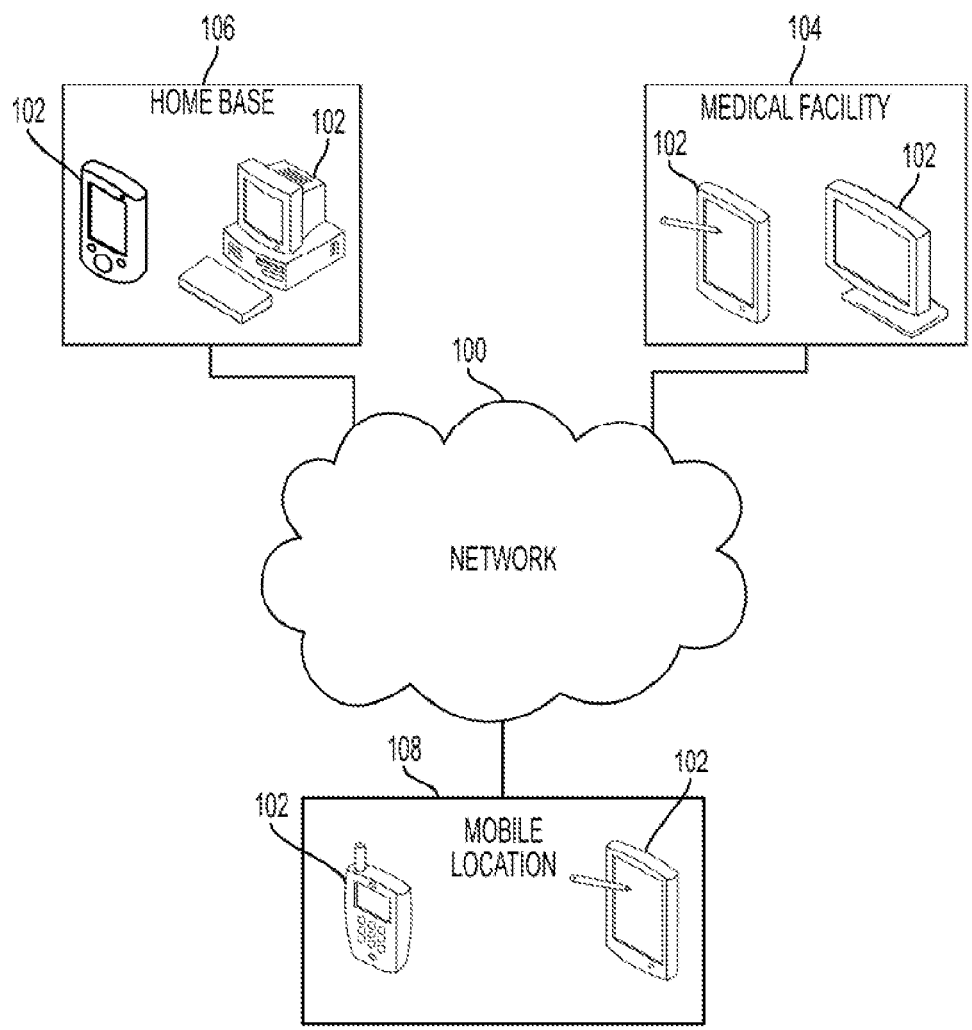
FIG. 2 is a schematic view of one embodiment of a network system including the system of FIG. 1.

Any of a variety of users can access, interact with, control, etc. a user interface from any of a variety of locations. For example, as shown in an embodiment illustrated in FIG. 2, the user interface can be accessible over a network 100 (e.g., over the Internet via cloud computing) from any number of client stations 102 in any number of locations such as a medical facility 104 (e.g., a hospital, an operating room (OR), a nurse's station, a medical device distribution facility, a medical device company, a hospital's sterilization, records, or billing departments, etc.), a home base 106 (e.g., a person's home or office, a surgeon's home or office, etc.), a mobile location 108, and so forth. The client station(s) 102 can access the user interface through a wired and/or wireless connection to the network 100 such that the user interface is displayed on a display screen thereof, e.g., an LCD (liquid-crystal display), ePaper, a touch screen, etc. In an exemplary embodiment, at least some of the client station(s) 102 can access the user interface wirelessly, e.g., through WiFi connection(s), which can facilitate accessibility of the user interface from almost any location in the world. Data can be transmitted wirelessly using an existing protocol such as 802.11 or a proprietary protocol, e.g., a protocol that optimizes power, data, and range for a particular use more than an existing protocol. As shown in FIG. 2, the medical facility 104 includes client stations 102 in the form of a tablet and a computer touch screen, the home base 106 includes client stations 102 in the form of a mobile phone having a touch screen and a desktop computer, and the mobile location 108 includes client stations 102 in the form of a tablet and a mobile phone, but the medical facility 104, the home base 106, and the mobile location 108 can include any number and any type of client stations. In an exemplary embodiment, the user interface can be accessible by an interface via a web address and/or a client application (also referred to herein as an "app").

It will be appreciated that the user interface can be accessible using one or more security features such that the aspects of the user interface available to any particular user can be determined based on the identity of the user and/or the location from which the user is accessing the user interface. To that end, each user can have a unique username, password, and/or other security credentials to facilitate access to the user interface. The received security parameter information can be checked against a database of authorized users to determine whether the user is authorized and to what extent the user is permitted to interact with the user interface, view stored information, and so forth. Examples of users who can be permitted to access a user interface include patients, potential patients, significant others, friends, and family members of patients or potential patients, surgical technicians, imaging technicians (e.g., x-ray technicians, MRI technicians, etc.), surgeons, nurses, hospital administrators, surgical equipment manufacturer employees, insurance providers, and operating room directors.

The devices, systems, and methods disclosed herein can be implemented using one or more computer systems, which as mentioned above are also referred to herein as interfaces and client stations.

Figure 3:
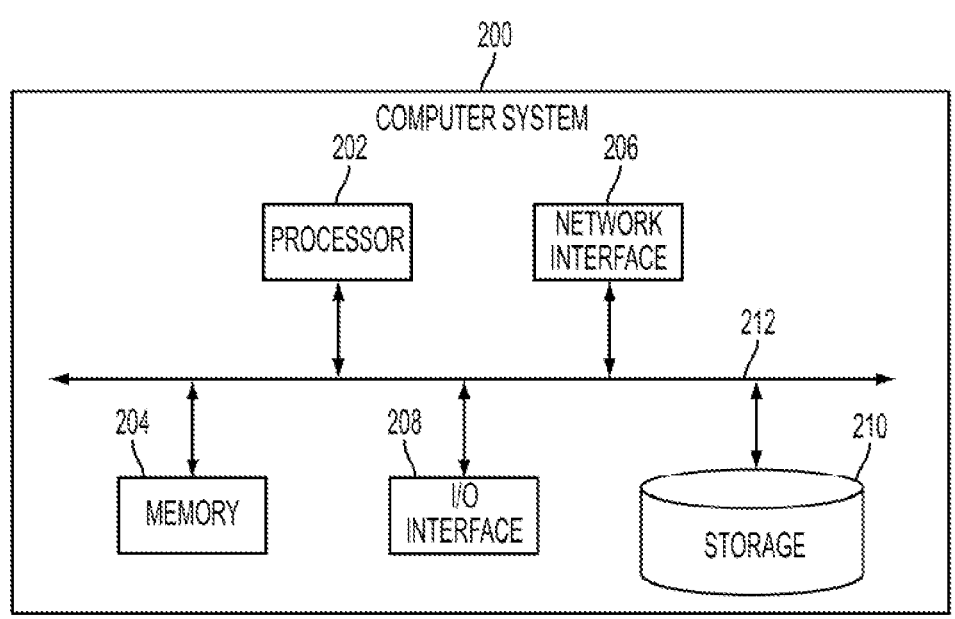
FIG. 3 is a schematic view of one embodiment of a computer system.

FIG. 3 illustrates one exemplary embodiment of a computer system 200. As shown in the illustrated embodiment, the computer system 200 can include one or more processors 202 which can control the operation of the computer system 200. The processor(s) 202 can include any type of microprocessor or central processing unit (CPU), including programmable general-purpose or special-purpose microprocessors and/or any one of a variety of proprietary or commercially available single or multi-processor systems.

The computer system 200 can also include one or more memories 204, which can provide temporary storage for code to be executed by the processor(s) 202 or for data acquired from one or more users, storage devices, and/or databases. The memory 204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 200 can be coupled to a bus system 212. The illustrated bus system 212 is an abstraction that represents any one or more separate physical busses, communication lines/interfaces, and/or multi-drop or point-to-point connections, connected by appropriate bridges, adapters, and/or controllers. The computer system 200 can also include one or more network interface(s) 206, one or more input/output (I/O) interface(s) 208, and one or more storage device(s) 210.

The network interface(s) 206 can enable the computer system 200 to communicate with remote devices, e.g., other computer systems, over a network, and can be, for example, remote desktop connection interfaces, Ethernet adapters, and/or other local area network (LAN) adapters. The I/O interface(s) 208 can include one or more interface components to connect the computer system 200 with other electronic equipment. For example, the I/O interface(s) 208 can include high speed data ports, such as universal serial bus (USB) ports, 1394 ports, Wi-Fi, Bluetooth, etc. Additionally, the computer system 200 can be accessible to a user, and thus the I/O interface(s) 208 can include display screens, speakers, keyboards, pointing devices, and/or various other video, audio, or alphanumeric interfaces. The storage device(s) 210 can include any conventional unit or medium for storing data in a non-volatile and/or non-transient manner. The storage device(s) 210 can thus hold data and/or instructions in a persistent state, i.e., the value is retained despite interruption of power to the computer system 100. The storage device(s) 210 can include one or more hard disk drives, flash drives, USB drives, optical drives, various media cards, diskettes, compact discs, and/or any combination thereof and can be directly connected to the computer system 200 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 3 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 200 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing Hypertext Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth.

The computer system 200 can also include a web server for generating and/or delivering the web pages to client computer systems.

In an exemplary embodiment, the computer system 200 can be provided as a single unit, e.g., as a single server, as a single tower, contained within a single housing, etc. The systems and methods disclosed herein can thus be provided as a singular unit configured to provide the various modules, display the various user interfaces, and capture the data described herein. The singular unit can be modular such that various aspects thereof can be swapped in and out as needed for, e.g., upgrade, replacement, maintenance, etc., without interrupting functionality of any other aspects of the system. The singular unit can thus also be scalable with the ability to be added to as additional modules and/or additional functionality of existing modules are desired and/or improved upon.

While some embodiments are described herein in the context of web pages, it will be appreciated that in other embodiments, one or more of the described functions can be performed without the use of web pages and/or by other than web browser software. A computer system can also include any of a variety of other software and/or hardware components, including, for example, operating systems and database management systems. Although an exemplary computer system is depicted and described herein, it will be appreciated that this is for sake of generality and convenience. In other embodiments, the computer system may differ in architecture and operation from that shown and described here.

Referring again to the system 10 of FIG. 1, the wireless bridge 14 can have a variety of sizes, shapes, and configurations. The wireless bridge 14 can include a base station 38 and a router 40, as in the illustrated embodiment. A person skilled in the art will appreciate, however, that the wireless bridge 14 can include these and/or other components to facilitate electronic communication, similar to that discussed above regarding the network interface 32. The base station 38 and/or the router 40 can, as mentioned above, be included as part of the accessory 12 or can be remotely located therefrom, such as at the patient's home, the patient's school, the patient's work office, the patient's doctor's office, the patient's day care center, etc. The accessory 12 can be configured to communicate with only one base station 38, or with a plurality of pre-approved or pre-registered base stations 38, which can help ensure that data regarding the patient 22 is not transmitted to an unauthorized area. Embodiments of wireless bridges are further discussed in Intl. App. No. PCT/US13/047507 (Intl. Pub. No. WO 2014/004437) entitled "Devices, Systems, And Methods For Adherence Monitoring And Patient Interaction" filed Jun. 25, 2013, which is hereby incorporated by reference in its entirety.

As mentioned above, any of a variety of users can access, interact with, control, etc. a user interface, with the user interface optionally being customized for a category of a particular user, such as any one or more of a relationship of the user to the person 22 (e.g., the patient, a family member of the patient, a care provider for the patient, etc.), a gender of the user, and an age of the user. The user interface can provide data regarding any one or more aspects of a system including an accessory, a consumable associated with the accessory, and a person associated with the consumable. In addition to providing data to a user, the user interface can be configured to accept user input, e.g., via an I/O device, and data input by the user can be stored in any one or more memories. For example, the user interface can be configured to prompt a user to enter data in response to a question regarding consumable administration that can help explain any anomalies, e.g., a question asking what the patient was doing or experiencing when emergency medication was administered (e.g., playing sports, sleeping, attending school class, suffering from allergies, etc.), etc., a question asking why a consumable dosage was missed, etc. An accessory's processor and/or a processor located remotely from the accessory can be configured to analyze input answers so as to "learn" patient behavior and incorporate the "learned" behavior into, e.g., recommendations regarding the patient's treatment plan and predictions of the patient's future behavior. The system can be configured to generate and provide a report providing results of analysis using data from the accessory, which can help the person 22 and/or one or more of the person's care providers (e.g., doctors, family members, etc.) evaluate the person's consumables usage, facilitate the development of questions tailored to the person's specific history, and/or facilitate comparison of the person's consumables usage with clinical trends. Embodiments of user interfaces that can be configured for use with a system including an accessory are described in more detailed in previously mentioned Intl. App. No. PCT/US13/047507.

The system 10 as a whole can be integrated with one or more external devices, such as a lung function device/peak flow meter. The data provided by the external device(s) can be combined with the data collected by the system 10, e.g., data gathered by the accessory 12 attached to a consumables dispenser, to provide a more comprehensive picture of the person's status, to perform additional analytics, and so on.

The accessory 12 can have a variety of sizes, shapes, and configurations. In general, the accessory 12 can be mechanical, e.g., a physical component including machinery and/or electrical elements. The accessory 12 can be configured to be removably and replaceably attached to the dispenser so as to allow the accessory 12 to be attached to the person's existing dispenser and/or to be removed from an empty dispenser and attached to another dispenser. Examples of the accessory include a cap configured to attach to an end of a dispenser, a band or strap configured to wrap at least partially around a dispenser, and a box configured to attach to a surface of a dispenser. As mentioned above, the accessory 12 can instead be integrally attached to a dispenser, such as by being integrally formed therewith during manufacturing of the dispenser before a consumer receives the dispenser.

The accessory 12 can include any one or more of an activation member 26, a sensor 28, an actuator 30, a network interface 32, a processor 34, and a power source 36. Each of the activation member 26, the sensor 28, the actuator 30, the network interface 32, the processor 34, and the power source 36 can have a variety of sizes, shapes, and configurations.

The activation member 26 can be configured to be activated when a consumable is dispensed from the dispenser, and in some embodiments, the activation member 26 can be configured to be automatically activated when the consumable is dispensed. In other words, the consumable being dispensed in its ordinary way can activate the activation member 26 such that a user of the dispenser need not perform any special action to activate the activation member 26. The activation member 26 can thus be integrated into the functionality of the dispenser, which can help the accessory 12 gather data regarding the consumable, as discussed further below. For example, the activation member 26 can be positioned at an end of a respiratory inhaler and can be configured to be pushed down by a user to push down a medication canister and release a metered-dose of respiratory medication from the inhaler such that, even without the accessory 12 attached thereto, the canister can be configured to be pushed down by a user to release a metered-dose of respiratory medication from the inhaler. The activation member 26 can thus be configured to move when the respiratory medication is dispensed.

The activation member 26 can include a depressible member. For example, the depressible member can include a button, e.g., a push button, but the depressible member can be in another form, such as a depressible switch or a force sensitive resistor. Pushing the accessory 12, e.g., pushing on an inhaler to release a consumable therefrom, can automatically activate the activation member 26 as well as cause the consumable to be released.

Another example of the activation member 26 includes a motion-sensitive member such as a motion sensor configured to sense movement of the accessory 12. For example, the motion-sensitive member can be positioned at an end of a respiratory inhaler (e.g., an asthma inhaler) and can be configured to be moved by a user to move the inhaler's medication canister to release a metered-dose of respiratory medication from the inhaler such that, even without the accessory 12 attached thereto, the canister can be configured to be moved by a user to release a metered-dose of respiratory medication from the inhaler, such that the motion-sensitive member can sense movement when the accessory 12 is pushed down. For another example, a first motion-sensitive member can be positioned on an exterior plastic container of a respiratory inhaler (e.g., an asthma inhaler), and a second motion-sensitive member can be positioned on a medication canister that is at least partially encased by the exterior plastic container and that is movable relative thereto when medication is dispensed. A difference in motion detected by the two motion-sensitive members can indicate that a consumable was dispensed. For another example, a first motion-sensitive member can be coupled to a consumables dispenser at a first location, and a second motion-sensitive member can be coupled to the consumables dispenser at a second, different location. The two motion-sensitive members can be configured to sense movement in different areas of the dispenser that can together provide sensed data indicative of a consumable being dispensed, e.g., movement sensed by a first motion-sensitive member coupled to a bottle cap and movement sensed by a second motion-sensitive member coupled to a main body of the bottle to which the cap is releasable attached.

When the activation member 26 is activated, thereby indicating that a consumable is being dispensed, the activation member 26 can be configured to activate or "wake up" the processor 34. The activation member 26 can thus be configured to trigger data gathering by the processor 34. The activation member 26 can be configured to "wake up" the processor 34 in a variety of ways, as will be appreciated by a person skilled in the art, such as by the activation member 26 being configured to cause an activation signal to be transmitted to the processor 34. The activation signal can cause the processor 34 to perform one or more functions in connection with dispensing of the consumable. For example, the activation member 26 can be configured to cause a circuit to close when the activation member 26 is in a depressed position. The circuit can correspondingly be open when the activation member 26 is in a non-depressed position. The closing of the circuit can cause an activation signal to be transmitted to the processor 34 and/or for a circuit within the processor 34 to be closed.

The activation of the activation member 26 can be enough to cause the processor 34 to perform function(s) in connection with dispensing of the consumable. However, in some embodiments, the processor 34 can be configured to perform the function(s) in connection with dispensing of the consumable in response to receipt of the activation signal only upon a secondary determination that consumable was dispensed. In other words, the processor 34 can be configured to check for false positives. The sensor 28 can be configured to facilitate the secondary determination. The sensor 28 can help eliminate false positives when, for example, the dispenser is within a backpack or other bag and is jarred against a side of the bag so as to unintentionally move the activation member 26 (e.g., partially depress the activation member 26, jostle the activation member 26 so as to register kinetic motion, etc.) and activate or "wake-up" the processor 34 even though a consumable was not actually dispensed.

The sensor 28 can have a variety of sizes, shapes, and configurations. The sensor 28 can be configured to sense at least one condition indicative of the consumable being dispensed from the dispenser. The sensor 28 can be configured to transmit data regarding its sensed parameter(s) to the processor 34, which can be configured to analyze the received sensed data to help determine whether a consumable was dispensed from the dispenser. In general, the processor 34 can be configured to determine if the sensed parameter is above or below a predetermined threshold amount for the sensed parameter and conclude based on that determination whether the sensed parameter indicates that a consumable was dispensed.

The accessory 12 can include any number of sensors 28. If the accessory 12 includes a plurality of sensors 28, the sensors 28 can be configured to sense at least two different parameters so as to provide a plurality of different factors to aid in the processor's secondary determination of the consumable being dispensed or not. For example, the accessory 12 can include a pressure sensor and a motion sensor. Alternatively, if the accessory 12 includes a plurality of sensors 28, each of the sensors 28 can be configured to sense a same parameter so as to provide a plurality of measurements of the parameter that can be compared with one another to assess whether a consumable was dispensed. For example, the accessory 12 can include a plurality of motion sensors.

The sensor 28 can be configured to continuously sense data, or the sensor 28 can be configured to sporadically sense data based on activation of the activation member 26. The sensor 28 continuously sensing data can help ensure that the sensor 28 has adequate data available each time the processor 34 is activated by the activation member 26. Continually sensing data can help the processor 34 "learn" ambient conditions of the dispenser, the accessory 12, and/or the consumable over time, which can help the processor 34 better distinguish false positives from actual instances of the consumable being dispensed. The sensor 28 can be configured to sporadically sense data by being triggered by the processor 34 to begin sensing. The processor 34 can be configured to provide such a trigger when the processor 34 is activated by the activation member 26. Sporadically sensing data can consume less power than continuously sensing data, which can help prolong a life of the accessory 12.

Examples of the sensor 28 include a motion sensor, a pH sensor, a temperature sensor, a pressure sensor, an audio sensor, an air pressure sensor, and a geographic location sensor. Various embodiments of the sensor 28 are described in previously mentioned Intl. App. No. PCT/US13/047507. Generally, the motion sensor (e.g., an accelerometer, a gyroscope, a magnetic field sensor, etc.) can be configured to sense motion (e.g., movement, shock, vibration, orientation, etc.) of the accessory 12, the pH sensor can be configured to sense a pH at a location where the consumable is dispensed from the dispenser, the temperature sensor can be configured to sense a change in temperature and/or humidity such as a change in temperature and/or humidity of the dispenser, the pressure sensor can be configured to sense a weight or pressure being exerted thereon, the audio sensor (e.g., a microphone, etc.) can be configured to sense a sound of consumable dispensing, and the geographic location sensor (e.g., a global positioning system (GPS) sensor, etc.) can be configured to sense a geographic location.

In some embodiments, an external device (e.g., a smartphone, etc.) can include a geographic location sensor that can provide geographic location information that can be used in combination with data sensed by the accessory's sensor 28 to help the processor 34 determine whether a consumable was dispensed from a dispenser to which the accessory is coupled. For example, if sensed kinetic motion from a motion sensor of the accessory 12 indicates motion indicative of consumable dispensing, and geographic location information from the external device indicates a predetermined location where the person 22 typically dispenses consumables (e.g., the person's home, an eating location such as the person's kitchen, the person's school cafeteria, a restaurant, etc.), then the processor 34 can be configured to determine that the consumable was dispensed. Conversely, if the geographic location information from the external device indicates a predetermined location where consumables are not typically dispensed (e.g., a highway, a subway line, etc.), the processor 34 can be configured to determine that, despite the motion data indicating a motion that could be indicative of a consumable being dispensed, a consumable was not dispensed, such as because the dispenser is being jostled during transportation.

Figure 21:
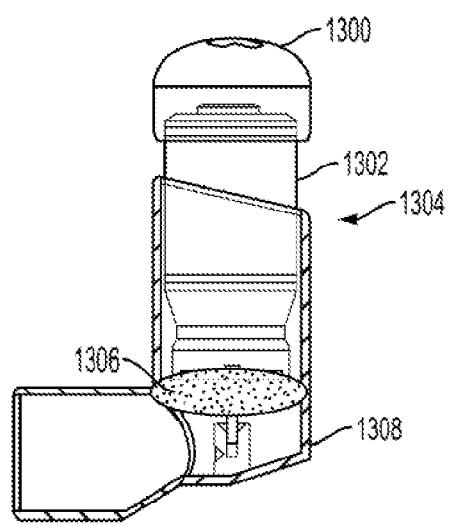
FIG. 21 is a side partially transparent view of another embodiment of a consumables dispenser in the form of a respiratory inhaler having first and second accessories attached thereto.

In some embodiments, the accessory's sensor 28 can include a pressure sensor, which can be attached to a consumables dispenser at a location where a weight or pressure is applied to the dispenser to dispense the consumable. In other words, a weight or pressure applied to dispense the consumable will also be applied to the pressure sensor. If the weight or pressure sensed by the pressure sensor is above a predetermined threshold amount of weight or pressure, a processor (e.g., the processor 34 on board the accessory and/or a remote processor that can communicate with the accessory) can be configured to determine that a consumable was dispensed from a dispenser coupled to the accessory because weight or pressure exerted on the pressure sensor increased enough to indicate that the consumable was dispensed, e.g., a canister was pushed down so as to dispense a consumable. The predetermined threshold amount of weight or pressure can vary based on the dispenser, as different dispensers can require a different amount of user-caused motion to dispense a consumable from the dispenser. For one example of a pressure sensor of an accessory, the pressure sensor can be positioned at a bottom of a medication canister containing respiratory medication that is pushed down to dispense medication therefrom, thereby exerting pressure on the pressure sensor disposed beneath the canister. Such a location of a pressure sensor is shown in the embodiment of FIG. 21, discussed further below, where an accessory 1306 including a pressure sensor is positioned at a bottom of a canister 1302. For another example of a pressure sensor of an accessory, the pressure sensor can be located on a cap of a pill bottle, e.g., on an internal surface thereof, and can be configured to be removed from the bottle when the cap is removed from the bottle, e.g., the cap is unscrewed, the cap is snapped off, etc. The cap being removed from the bottle can release pressure being exerted on the cap by the bottle. In other embodiments, the pressure sensor of the accessory can be located on the pill bottle instead of on the cap such that removal of the cap from the bottle can release pressure being exerted thereby on the pressure sensor.

For another example of a pressure sensor of an accessory, the pressure sensor can be positioned at a portion of a consumables dispenser that typically rests on a table, shelf, or other surface when the dispenser is not in use. When resting on a surface, a weight or pressure will be continuously applied to the pressure sensor. If the weight or pressure sensed by the pressure sensor decreases by at least a predetermined threshold amount of weight or pressure, a processor (e.g., the processor 34 on board the accessory and/or a remote processor that can communicate with the accessory) can be configured to determine that the consumable was dispensed because weight or pressure exerted on the pressure sensor by the surface was removed, e.g., one or more pills were removed from a pill bottle having the accessory coupled to a bottom thereof that typically rests on a surface when the bottle is not in use. The predetermined threshold amount of weight or pressure can vary based on the dispenser, because different consumables can have different weights and because different prescriptions can require different amounts of consumables to be dispensed at a time. Such a location is shown, for example, in the embodiment of FIG. 19, discussed further below, with an accessory 1100 including a pressure sensor being positioned at a cap 1104 on which a tube 1102 typically rests when the tube 1102 is not in use.

In some embodiments, the sensor 28 can be disposed adjacent an opening of the dispenser through which the consumables can be dispensed. A change in a condition adjacent the opening can be detected by the sensor 28, thereby indicating that a consumable was dispensed. For example, the sensor 28 can be disposed adjacent a mouthpiece of a consumables dispenser, such as a mouthpiece of a respiratory inhaler, through which the consumables can exit the dispenser so as to be dispensed. In an exemplary embodiment, the sensor 28 can be positioned within a pathway within the dispenser through which the consumable passes before exiting the dispenser. The sensor 28 can thus be protected from inadvertent damage by being exposed outside the dispenser and/or can be less likely to detect ambient conditions outside the dispenser that may cause registration of a false positive of a consumable being dispensed. Such a location is shown, for example, in the embodiment of FIG. 22, discussed further below, with an accessory 1400 positioned adjacent a mouthpiece 1402 within a consumables pathway 1406.

One example of a sensor configured to sense at least one condition indicative of the consumable being dispensed from the dispenser is an air pressure sensor. Some types of consumables can cause air pressure adjacent the consumable's exit area from the dispenser to temporarily change when the consumable is dispensed from the dispenser. The air pressure sensor can be positioned adjacent a consumable exit area such that the consumable passes thereby and/or therethrough when the consumable is dispensed from the dispenser. For example, respiratory medication administered through a mouthpiece of a medication dispenser can cause air pressure to temporarily change, e.g., increase, at the mouthpiece when medication is dispensed therefrom. The air pressure sensor can thus be located adjacent the mouthpiece. Such a location is shown, for example, in the embodiment of FIG. 22 with the accessory 1400 positioned adjacent the mouthpiece 1402 within the consumables pathway 1406.

If air pressure sensed by the air pressure sensor is outside a predetermined air pressure range, is above a predetermined air pressure temperature, and/or changes by more than a predetermined threshold amount, a processor (e.g., the processor 34 on board the accessory and/or a remote processor that can communicate with the accessory) can be configured to determine that a consumable was dispensed from a dispenser to which the accessory is coupled because the air pressure changed enough to indicate that the consumable was dispensed. For example, at least some respiratory medications dispensed from an inhaler can cause air pressure within the dispenser's mouthpiece to temporarily change, e.g., increase, in air pressure. The air pressure sensor can thus facilitate determination that medication was dispensed from the dispenser. For another example, some consumable dispensers are pressurized, such as canisters of respiratory inhalers, and change in air pressure when damaged, e.g., decrease in air pressure if the canister cracks or otherwise breaks. The air pressure sensor can facilitate determination of dispenser damage by detecting a decrease in air pressure since such a decrease would typically only be indicative of an error such as dispenser damage.

Another example of a sensor configured to sense at least one condition indicative of the consumable being dispensed from the dispenser is a temperature sensor. Some types of consumables can cause a temperature adjacent the consumable's exit area from the dispenser to temporarily change when the consumable is dispensed from the dispenser. The temperature sensor can be positioned adjacent consumable exit area such that consumable passes thereby and/or therethrough when the consumable is dispensed from the dispenser Similar to that discussed above regarding the air pressure sensor, if the temperature sensed by the temperature sensor changes by more than a predetermined threshold amount, a processor can be configured to determine that a consumable was dispensed from a dispenser to which the accessory is coupled because the temperature changed enough to indicate that the consumable was dispensed and/or that an error such as dispenser damage occurred. For example, respiratory medication administered through a mouthpiece of a medication dispenser can cause a temperature adjacent the mouthpiece to temporarily change, e.g., decrease, at the mouthpiece when medication is dispensed therefrom. The temperature sensor can thus be located adjacent the mouthpiece. Such a location is shown, for example, in the embodiment of FIG. 22 with the accessory 1400 positioned adjacent the mouthpiece 1402 within the consumables pathway 1406.

In some embodiments, the sensor configured to sense at least one condition indicative of the consumable being dispensed from the dispenser can include a motion sensor. A change in kinetic motion of the accessory, and hence the dispenser to which the accessory is attached, can indicate that a consumable was dispensed from the dispenser. For example, if the motion sensor is attached to a pill box and the motion sensor senses that the box was titled, a processor (on-board the accessory and/or located off-board from the accessory) in communication with the motion sensor can infer that a consumable was dispensed from the pill box. In addition, as discussed herein, the processor can be configured to consider one or more additional data that can be used to further confirm or to refute that a consumable was dispensed, such as information from a second motion sensor attached to the pill box. The motion sensor can be configured to be omnidirectional, e.g., sense motion in every direction.

In an exemplary embodiment, the motion sensor can be three-dimensional, e.g., sense motion in three directions such as along x, y, and z axes. If the motion sensed by the motion sensor is above a predetermined threshold amount of motion, a processor (on-board the accessory and/or located off-board from the accessory) can be configured to determine that a consumable was dispensed because the accessory including the sensor moved enough to cause the consumable to be dispensed from the dispenser to which the accessory is attached. The predetermined threshold amount of motion can vary based on the dispenser, as different dispensers can require a different amount of user-caused motion to dispense a consumable from the dispenser. Accessories including motion sensors are shown, for example, in the embodiments of FIGS. 14-20 and 23-26, which are discussed further below.

In some embodiments, the motion sensor can be configured to sense motion (e.g., tilting, shaking, rotation, a jolt, etc.) and to sense orientation. If the motion sensor is configured to sense orientation, a processor (on-board the accessory and/or located off-board from the accessory) can be configured to determine whether the sensed orientation matches a predetermined orientation indicative of a consumable-dispensing position of the dispenser. For example, respiratory inhalers are typically held in an upright position when medication is dispensed in order for the dispenser to be comfortably held by hand with the dispenser's mouthpiece at a person's mouth. The motion sensor sensing this orientation can thus be indicative of a consumable being dispensed. In some embodiments, the motion sensor sensing this orientation for at least a predetermined minimum amount of time can be indicative of the consumable being dispensed, while the motion sensor sensing this orientation for less than the predetermined minimum amount of time can be dismissed as not being indicative of a consumable being dispensed, e.g., because the dispenser was only briefly in that orientation while being dropped into a person's purse. For another example, a type of the motion sensed can be indicative of whether a consumable was dispensed, such as a small vibration typically not being indicative of dispensing, but a sensed motion that corresponds with lifting a dispenser, then tilting the dispenser, and then placing the dispenser back to its original position typically indicates dispensing.

In some embodiments, the motion sensor can be positioned on an external surface of a consumables dispenser, such as a strap or band that can be wrapped around an external surface of the dispenser. The accessory including the motion sensor can thus be retrofitted to existing consumable dispensers without requiring any modification of the dispenser (other than the simple attachment of the accessory thereto).

In some embodiments, the motion sensor can be included as part of a strap or band configured to attach to a consumables dispenser, and the strap or band can be configured to sense one or more environmental factors (e.g., temperature, humidity, vibration, time of day, etc.). Sensed data regarding the one or more environmental factors can be used to help determine whether motion detected by the motion sensor is actually indicative of a consumable being dispensed from the dispenser.

The actuator 30 can have a variety of sizes, shapes, and configurations. The actuator 30 can be configured to indicate to a user, e.g., to the person 22, a care provider for the person 22, etc., that a predetermined condition has occurred. The predetermined condition can reflect that action by the user is needed, such as the patient 22 consuming the consumable (e.g., taking a pill, applying cream, taking a dose of medication, etc.), the dispenser being replaced due to a lot amount of consumables remaining therein, or the dispenser being replaced due to no consumables remaining therein. The predetermined condition can occur without any user action, such as a scheduled dose of the consumable not being taken and data being transmitted from the accessory 12 to the wireless bridge 14. The processor 34 can be configured to actuate one or more of the actuators 30 in response to the processor 34 detecting occurrence of the predetermined condition, as discussed further below. Examples of the actuator 30 include a light (e.g., an LED, a fluorescent material, etc.) configured to illuminate, a speaker configured to output an audible sound, a vibration element configured to vibrate so as to cause palpable and/or audible vibration of the accessory 12 and/or the dispenser, a temperature-changing element configured to temporarily heat and/or cool so as to cause a palpable change in temperature of the accessory 12 and/or the dispenser, and a display screen configured to display text and/or images as a message to the user. If the actuator 30 includes a light, the accessory 12 can include the actuator 30 at a location configured to make the light visible from all vantage points of the accessory 12. For example, the actuator 30 can include a plurality of lights arranged around a full perimeter of the accessory 12, e.g., arranged equidistantly around the perimeter.

The accessory 12 can include any number of actuators 30, e.g., zero, one, two, three, etc. If the accessory 12 includes a plurality of actuators 30, in an exemplary embodiment, each of the actuators 30 can be configured to provide a different type of notification than at least one other of the actuators 30, e.g., a plurality of actuators 30 including at least one light and at least one speaker, so as to allow the accessory 12 to provide a plurality of different notifications when a consumable is due and/or to provide a different type of notification upon different types of predetermined conditions, a light of a first color and one vibration element for a consumable being due, a light of a second color for a consumable in the dispenser running low and a blinking light of the second color for a consumable in the dispenser being depleted, a blinking light when a dose is missed and a notification such as an email, text message, or phone call (which can be a live phone call or an automated phone call and can include leaving a voicemail or other recorded message) being sent to a location remote from the dispenser indicating that the dose was missed, etc.

The accessory 12 can be configured to cause a notification to be transmitted to a location remote from the dispenser instead of or in addition to a notification being provided via the actuator 30 at the dispenser. Providing a remote notification can facilitate supervision of the person 22 and/or management of the person's treatment plan. For example, if the person 22 is a child, it can be beneficial to notify the user 24 associated with the person 22 upon occurrence of certain events to help make the user 24 aware of the person's status so the user 24 can take any appropriate action in real time and/or at a later time.

For another example, if a dose of a consumable is due, the processor 34 can be configured to cause a first notification to be provided to the person 22 via the actuator 30 at the dispenser and to cause a second notification to be provided to the user 24, who may be at a location remote from the person 22. The user 24 can then decide whether to independently contact the person 22 as a secondary reminder to take the consumable.

For yet another example, if the processor 34 determines that a consumable was dispensed outside of the person's predetermined schedule, the processor 34 can be configured to cause a notification such as an email, text message, or phone call to be provided to the user 24, who, given this atypical use of the consumable, may be the person's care provider or be able to contact the person's medical care provider as the person's parent or guardian. If multiple off-schedule doses are detected, the person's care provider may choose to contact the person 22 (or an adult contact for the person 22 if the person 22 is a child) to discuss possible changes to the person's health and/or to the person's treatment plan.

For still another example, if the processor 34 determines that the consumable is running low, the processor 34 can be configured to cause a notification such as an email, text message, or phone call to be provided to the user 24, such as the person's doctor or pharmacist, who can begin processing a new supply of consumables for the person 22 before the patient's current consumables are depleted.

For another example, if a consumable is not dispensed within a predetermined period of time after a notification is provided indicating that a scheduled dose of the consumable is due, the processor 34 can be configured to cause a missed dosage notation to be saved in the accessory's memory, and the wireless bridge 14 can be configured to wirelessly transmit the stored missed dosage notation to an external device such as the database 18. The missed dosage notation can be included as part of adherence data and/or incentives data provided on a user interface, discussed further below. An external device, e.g., the interface 20, can be configured to determine that a dose was missed without the processor 34 providing any notice thereof, such as by the external device being configured to detect that notice of an expected dose was not taken, e.g., notice of a consumable being dispensed at a scheduled date/time was not received at the external device from the accessory 20.

In some instances, the person 22 may have multiple consumable dispensers, each of the dispensers having the same consumable contained therein. For example, the person 22 may have multiple containers of the same consumable each kept in a different location, e.g., home, work, car, etc., for easy accessibility when use of the consumable is needed. Each of the multiple consumable dispensers can have an accessory coupled thereto. Each of the accessories can be categorized in the system 10 as clones of one another so as to be linked together as being associated with the person 22 for a specific consumable, e.g., for a specific prescription medication. Thus, when a dose of the consumable is due according to a predetermined dosage schedule, the dose will likely not be dispensed from each of the dispensers containing the consumable. Instead, the dose will likely be dispensed from only one of the dispensers, or none of the dispensers if the dose is missed. If any one of the dispensers having the "cloned" accessories coupled thereto dispenses the scheduled dose, the dose can be considered to have been consumed on schedule. If none of the dispensers having the "cloned" accessories coupled thereto dispenses the scheduled dose, the dose can be considered to have been missed. The system 10 can thus be less likely to register false instances of missed dosages and/or less likely to transmit a notification to the person 22 and/or other person that a dose was missed when the dose was actually dispensed.

In some embodiments, in order to stop a notification (e.g., stop a light from blinking, stop a consumables dispenser from vibrating, etc.), a predetermined action must be taken in response to the predetermined condition that triggered the notification. In this way, certain user actions can be more likely to happen within a short amount of time. For example, if the predetermined condition includes a dose of a consumable being due, the notification can be configured to be provided (e.g., a light continually blinks on and off, an audio tone sounds on and off, a light continually glows, etc.) until dispensing of the consumable is detected. In some embodiments, in the absence of the predetermined action being taken within a predetermined amount of time from the notification being first provided, the notification can be configured to stop after the predetermined amount of time, which can help conserve power (e.g., not require an endlessly glowing light, etc.) and/or can compensate for situations in which it may not be currently possible for the person 22 to take the consumables dose.

The processor 34 can be configured to control one or more components of the accessory 12. The processor 34 can have a variety of sizes, shapes, and configurations, as discussed above. The processor 34 in the illustrated embodiment is shown as a microcontroller, but the processor 34 can include any of a variety of elements, as mentioned above. The processor 34 can, as will be appreciated by a person skilled in the art, include a timer configured to count time and/or a memory configured to store data. Alternatively, the timer and/or the memory can be included as part of the accessory 12 but be external components to the processor 34.

The processor 34 can be configured to cause gathered data to be stored in the memory and to cause stored data to be transmitted to an external device, e.g., wirelessly transmitted via the wireless bridge 14 across the network 16 to the interface 20 and/or the memory 18. The memory 18 in the illustrated embodiment includes a database, but as discussed above, the memory 18 can include any one or more memory technologies. The interface 20 in the illustrated embodiment includes a client station in the form of a distributed computer system (e.g., a phone, a computer, etc.), but the interface 20 can include any form of client station.

The processor 34 can be configured to transmit stored data to the interface 20 and/or the memory 18 on a predetermined transmission schedule, e.g., a schedule stored in the memory and time-tracked using the timer, in response to occurrence of a predetermined condition, and/or in response to a data request signal to the processor 34 from an external device. The processor 34 can be configured to delete transmitted data from the memory in response to the data having been transmitted, which can help free space for new data, the processor 34 can be configured to delete transmitted data on a regular deletion schedule (e.g., at the top of each hour, at the end of a day, at the end of a week, twice daily, etc.), or the processor 34 can be configured to delete transmitted data as needed for storage space. The processor 34 can be configured to maintain all data until the data is transmitted to an external device, which can help prevent data loss. The processor 34 can be configured to mark data stored in the memory as having been transmitted to an external device, which can facilitate clearing of the accessory's memory and/or help ensure that data is not unnecessarily repeatedly transmitted to an external device.

Various types of data can be received and stored by the processor 34. For example, data sensed by the sensor 28 can be received and stored. For another example, data regarding occurrences of predetermined conditions can be stored. Examples of predetermined conditions include a consumable being dispensed (e.g., as triggered by activation of the activation mechanism 26 and/or as confirmed by data from the sensor 28), low power source 36 power, power source 36 depletion, a consumable not being dispensed in accordance with a predetermined schedule, and device component failure. The processor 34 can therefore be configured to receive, store, and transmit a relatively complete picture of the patient's consumable usage and of a functional status of the dispenser and a functional status of the accessory 12. Data transmitted by the processor 34 can be analyzed by and/or viewed on the interface 20, as discussed further below.

The processor 34 can be configured to maintain a running tally of a total amount of consumables dispensed from the dispenser. In this way, the processor 34 can be configured to determine when the dispenser is running low on the consumable and/or when all the consumables have been dispensed from the dispenser. For example, some types of dispensers, such as respiratory inhalers, can be configured to dispense a predetermined amount of medication each time the medication is dispensed therefrom. The processor 34 can be configured to maintain the running tally of a total amount of consumables dispensed from the dispenser by adding a predetermined value to the previously logged total amount each time a consumable is determined to have been dispensed from the dispenser. For another example, the accessory 12 can be configured to detect an amount of a consumable dispensed, e.g., by using the sensor 28, and to subtract the measured amount from a previously stored total amount of consumables in the dispenser to arrive at a current total amount of consumables in the dispenser.

The processor 34 can be configured to provide a warning to a user when the processor determines that the dispenser is running low on consumables and/or when all consumables have been dispensed from the dispenser. Providing warnings about low/no consumables remaining can help the user effectively manage reordering and replacement of consumables. The processor 34 can be configured to provide the warning by actuating the actuator 30.

The processor 34 can be configured to actuate the actuator 30 by transmitting a signal thereto. In response to the triggering signal from the processor 34, the actuator 30 can be configured to provide an audible and/or palpable signal to a user, e.g., to the patient 22, indicating one or more predetermined conditions. One example of the predetermined condition is the low consumables warning mentioned above, and another example of the predetermined condition is the consumables depleted warning also mentioned above.

Another example of the predetermined condition is a notification when a dosage of the consumable is due. In other words, the accessory 12 can be configured to provide notice to a user, e.g., to the patient 22, that a consumable needs to be taken in order to adhere to a predetermined schedule. The accessory 12 providing the notification can allow the dispenser itself to play a role in a person's regimen, which can help reduce the need for the person 22, the person's family, the person's doctor, etc. to maintain and monitor an external notification system, such as watch alarms, alarms on a mobile device, phone calls to the patient, text messages to the patient's mobile phone, etc.

The processor 34 can be configured to determine that a dosage of a consumable is due in a variety of ways. A predetermined schedule for the person 22 can be accessible to the processor 34, e.g., stored in a memory included in the accessory 12 or stored in an external memory accessible via the network 16, such as the memory 18. The predetermined schedule can, as will be appreciated by a person skilled in the art, be specific to the person 22 as determined by the person 22 and/or the person's doctor or other care provider, or the predetermined schedule can be dictated by a manufacturer of the consumable. The accessory 12 can be configured to register itself, e.g., with the memory 18, when purchased and/or when attached to a dispenser so as allow the predetermined schedule to be transmitted to the accessory 12, e.g., from the memory 18. This registration can facilitate identification of "clone" accessories. The accessory 12 can be configured to detect attachment and detachment thereof from a dispenser, as discussed further below, which can facilitate registration of the accessory 12 when attached to the dispenser. The processor 34 can be configured to determine when a consumable is due according to the predetermined schedule based on time counted by the timer. The accessory 12 can thus be configured as a self-contained monitoring unit able to notify the user that a consumable is due to be taken regardless of the accessory's location relative to the interface 20 and/or other external device. Alternatively, or in addition, an external device such as the interface 20 can be configured to determine when a dosage of the consumable is due for the person 22 in a similar way and transmit a signal to the accessory 12 via the network 16. The signal can cause the actuator 30 to be actuated. Allowing the external device to trigger the actuator 30 can provide backup functionality to the processor 34 and/or can help move processing resources off-board from the accessory 12, which can help reduce cost and/or help reduce a size of the accessory 12.

Another example of a predetermined condition is data being transmitted from the accessory 12 via the network interface 32. Providing notice to the user that data is being transmitted can help explain why the accessory 12 may be buzzing or otherwise making a noise not typically associated with the dispenser. Similarly, another predetermined condition is data being transmitted to the accessory 12 via the network interface 32, such as an update to the patient's predetermined schedule stored onboard the accessory 12.

As mentioned above, a predetermined condition can include the power source 36 running low, thereby indicating that the accessory 12 is due for removal from the dispenser and replacement with another accessory. Similarly, another predetermined condition is the power source 36 being depleted of available power.

As mentioned above, a predetermined condition can include failure of any component of the accessory 12, such as a failure of the sensor 28 or the actuator 30, thereby indicating that the accessory 12 should be removed from the dispenser and replaced with another accessory. The processor 34 can be configured to detect failure of a component of the accessory 12, such as by being programmed to regularly query component(s), as will be appreciated by a person skilled in the art, and, based on a response received from the queried component, including whether a response was received or not, determine whether the component is properly functioning.

The network interface 32 can be configured to facilitate electronic communication of the accessory 12 with one or more external devices such as the wireless bridge 14. The network interface 32 can have a variety of sizes, shapes, and configurations, as discussed above. Although the network interface 32 is illustrated as a radio and as being in electronic communication with the wireless bridge 14 in the illustrated embodiment, the network interface 32 can be a component other than a radio and can be configured to be in electronic communication with a wireless bridge and/or any number of other components to facilitate communication over the network 16. The network interface 32 can be configured to communicate using long-range, low frequency/low power/low bandwidth radio communication using a proprietary, an open source, or a mesh protocol.

The power source 36, e.g., one or more batteries, one or more solar panels, one or more piezo elements, one or more inductively charged power elements, etc., can have a variety of sizes, shapes, and configurations. The power source 36 can be configured to provide power to one or more of the accessory's components, e.g., to the sensor 28, the processor 34, the wireless bridge 14, the actuator 30, etc. In some embodiments, an accessory can lack a power source and instead be powered by an external power source, such as a power source wired to the accessory via wired connection or a power source configured to telemetrically provide power when moved into proximity of the accessory. In some embodiments, an accessory can include an on-board power source, as in the illustrated embodiment of FIG. 1, configured to provide power to only a portion of the accessory's on-board components, and the accessory can be configured to have another portion of the accessory's on-board components be powered by an external power source. Providing power with an external power source can help reduce a size of the accessory and/or free space for other components.

In some embodiments, the power source 36 can be configured to move between a first state in which the power source 36 provides a first amount of power to components of the accessory 12 and a second state in which the power source 36 provides a second, greater amount of power to the components of the accessory 12. The power source 36 can thus be configured to conserve power by being in the first state when the greater amount of power provided in the second state is not necessary for proper functioning of the accessory 12. Embodiments of power sources being configured to move between first and second states are described in more detail in previously mentioned Intl. App. No. PCT/US13/047507.

In some embodiments, the accessory 12 can include energy-harvesting technology (solar, piezo, etc.) configured to increase a life of the power source 36, e.g., to increase a battery life of a battery when the power source 36 includes a battery.

The accessory 12 can include a housing 42 configured to house the activation member 26, the sensor 28, the actuator 30, the network interface 32, the processor 34, the power source 36, and the wireless bridge 14. The accessory 12 as a singular unit including the housing 42 and all components housed therein can be configured to be removably and replaceably attached to the dispenser, thereby allowing simple attachment of a single piece to the dispenser to attach the accessory 12 thereto. The accessory 12 can thus lack any required user assembly and can be easily attached to a dispenser by adults and by at least older children.

The housing 42 can have a variety of sizes, shapes, and configurations and can be formed from one or more materials. In an exemplary embodiment, the housing 42 can be formed from one or more polymers (e.g., thermoplastic elastomers (TPE), acrylonitrile-butadiene-styrene (ABS), etc.) and can be non-toxic. The housing 42 can be rigid or, as in the illustrated embodiment, have some degree of flexibility, which can facilitate depression of the activation member 26, as discussed further below. The housing 42 can be transparent or translucent so as to allow a light to visibly shine therethrough, as also discussed further below. The housing 42 can be waterproof so as to help protect the various components housed therein from moisture damage. The housing 42 can be permanently closed or sealed (e.g., closed or sealed under conditions of ordinary end-user use) so as to help prevent tampering with and/or inadvertent damage to the various components housed therein. The housing 42, and hence the accessory 12, can be configured to be disposable, e.g., thrown out or recycled. An accessory can, in some embodiments, be non-removably attached to a dispenser, in which case the accessory can be configured to be disposed of with the dispenser.

The housing 42 is shown in the illustrated embodiment as housing all of the activation member 26, the sensor 28, the actuator 30, the network interface 32, the processor 34, the power source 36, and the wireless bridge 14, but one or more of these components can be disposed in at least one other housing configured to attach to the dispenser similar to that discussed herein regarding the housing 42. For example, the wireless bridge 14 can be housed in a second housing (not shown) of the accessory 12, which can help facilitate hardware and/or software repair and/or upgrades related to electronic communication that otherwise do not substantially affect operation of the accessory 12. The second housing can be made, configured, and used similar to that discussed herein regarding the housing 42.

The accessory 12 can be configured to be attached to the dispenser in a variety of ways. The accessory 12 can include an attachment mechanism configured to engage the dispenser and removably and replaceably attach the accessory 12 thereto. Examples of the attachment mechanism include a magnet configured to magnetically attach the accessory 12 to a magnet included in or a metallic material of the dispenser, Velcro®, a cavity formed in the accessory configured to fit around a portion of the dispenser in a press fit, a strap or band configured to be tied to secure the accessory 12 to the dispenser, a strap or band configured to elastically secure the accessory 12 to the dispenser similar to a rubber band, a clip configured to clip the accessory 12 to the dispenser, and a guide track configured to slidably receive a portion of the dispenser therein. The attachment mechanism as a magnet can be particularly effective for use with pressurized dispensers, such as respiratory inhalers, which are typically metallic containers. The attachment mechanism being attachable to the dispenser by press fit can help prevent mis-attachment of the accessory 12 to the dispenser because the cavity can be configured to be attachable to the dispenser in one location via the press fit, e.g., the cavity being configured to only accommodate one unique portion of the dispenser. The accessory 12 can thus be keyed to the dispenser so as to be attachable thereto in a predetermined orientation relative thereto, as further described in previously mentioned Intl. App. No. PCT/US13/047507. The accessory 12 can be included as part of a kit including a plurality of differently sized and/or differently shaped members (e.g., flexible rings, rigid rings, etc.) configured to be selectively attached to the accessory 12 to facilitate press fit of the accessory 12 to a particular dispenser. For example, one of the members having a size and shape corresponding to a circular size of an end of a respiratory inhaler can be inserted into a cavity of an accessory in the form of a cap so as to be seated in a groove formed therein. The member can be configured to form a press fit with the inhaler when the cap is attached thereto. The attachment mechanism being an adjustable member, such as a strap or band, can facilitate attachment of the accessory 12 to differently sized and/or irregularly shaped dispensers. In some embodiments, the adjustable member can be configured to dynamically adjust to a size and shape of the dispenser to which the adjustable member is attached, such as by being an elastic member. In some embodiments, the adjustable member can be configured to be manually adjustable to be securely attached to a dispenser, such as by being adjustable similar to a belt with a hook and release mechanism or a slidably adjustable member.

The attachment mechanism can allow the accessory 12 to be replaceably and removably attached to the dispenser without requiring any modification of the dispenser by the end-user or by a designer or manufacturer of the dispenser to accommodate the accessory 12. In this way, the accessory 12 can be used with nearly any consumables dispenser regardless of whether or not the dispenser was made for use with the accessory 12. Examples of attachment mechanisms that can allow for such attachment include a magnet, a cavity, and a strap or band. Other attachment mechanisms, such as a magnet or Velcro®, may require a modification of the dispenser to allow attachment of the accessory 12 thereto, such as by attaching a magnet or Velcro® to the dispenser using a self-stick adhesive.

A consumables dispenser to which the accessory 12 is removably and replaceably attached can be configured to dispense a consumable whether or not the accessory 12 is attached thereto. The consumables dispenser can thus be available to the person 22 for use even if an unexpected error occurs with the accessory 12, e.g., the accessory 12 is accidentally broken, the person 22 accidentally forgets to attach the accessory 12 to a new dispenser, etc., and the person 22 will not have to miss any required doses of the consumable due to the accessory error. The accessory 12 being configured to be replaceably and removably attached to a consumables dispenser can facilitate this maintained functionality of the dispenser. FIGS. 4, 7, and 14-26, which are discussed further below, illustrate embodiments of accessories configured to be coupled to consumables dispensers that can properly dispense consumables whether or not the accessory is attached thereto.

In some embodiments, the accessory 12 can include a grip mechanism configured to facilitate attachment of the attachment mechanism to the consumables dispenser. The grip mechanism can be configured to deform when the attachment mechanism is attached to the dispenser, which can help form a secure interference fit between the accessory 12 and the dispenser, can compensate for differently sized dispensers, and/or can compensate for an uneven dispenser surface to which the accessory 12 is coupled. For example, the grip mechanism can include protrusions extending radially inward from a cavity formed in the accessory 12 and being configured to deform when the dispenser is seated in the cavity. For another example, the grip mechanism can include a textured surface on an interior surface of a strap or band configured to engage an exterior surface of the dispenser.

A consumables dispenser to which an accessory can be coupled can include a physical dose counter or other dose counting mechanism, as will be appreciated by a person skilled in the art. In some embodiments, the physical dose counter or other dose counting mechanism can be linked to or integrated with the accessory. For example, the physical dose counter can be located at a bottom of the dispenser, and an accessory can be linked to or integrated with the physical dose counter or other dose counting mechanism so as to also be located at the bottom of the dispenser. If the linked or integrated accessory is configured to be removably and replaceably coupled to the dispenser, the physical dose counter or other dose counting mechanism can be removed and replaced with the accessory. In some embodiments, the accessory can be a separate element from the physical dose counter or other dose counting mechanism In such a case, the accessory and the physical dose counter or other dose counting mechanism can be located at a same location relative to the dispenser, e.g., both at a top thereof, or can be located in different locations relative to the dispenser, e.g., one on a top of the dispenser and one of a side of the dispenser.

FIGS. 4-6 illustrate one embodiment of an accessory 302. The accessory 302 is shown in FIGS. 4 and 5 removably and replaceably attached to a dispenser 304 and is shown in FIG. 6 as a standalone element unattached to any dispenser. The dispenser 304 of FIGS. 4 and 5 is a respiratory inhaler that includes a housing 312 and a medication canister 314 removably and replaceably seated in the dispenser housing 312 and containing a medication for treating a respiratory condition such as asthma, but as mentioned above, an accessory can be configured to attach to a variety of different types of dispensers containing different types of consumables.

A housing 300 of the accessory 302 can be a cap, as in the illustrated embodiment of FIGS. 4-6. The cap can be configured to removably and replaceably attach to a portion of the dispenser 304, such as to an end of the canister 314 containing the consumable and being configured to be pressed by a user to dispense the consumable from the dispenser. The accessory 302 can thus be configured to be depressed to cause consumable to be dispensed from an output 306 of the dispenser 304 similar to how the consumable would be dispensed from the dispenser 304 without the accessory 302 attached thereto. The accessory 302 can thus be relatively seamlessly integrated into a person's familiar use of the dispenser 304. The accessory 302 can include a printed circuit board (PCB) (not shown), which can be engaged in response to the pressing of the accessory 302 to facilitate a determination as to whether a consumable was dispensed from the dispenser 304, as described in more detail in previously mentioned Intl. App. No. PCT/US13/047507. In general, the PCB can be coupled to the accessory's processor on-board the accessory, or the PCB can be configured to cooperate with at least one off-board component, e.g., a CPU control store (CCS) module located outside the cap.

In the illustrated embodiment, the attachment mechanism of the accessory 302 includes a cavity 308 formed in the housing 300. The cavity 308 can be configured to receive a portion of the dispenser 304 therein, e.g., an end portion of the dispenser 304. As in the illustrated embodiment, the cavity 308 can be configured to only be attachable to that one portion of the dispenser 304, which can help ensure that the accessory 302 is properly attached to and used with the dispenser 304 because there is only one option to the user in choosing where to attach the accessory 302 to the dispenser 304.

The housing 300 can include a symbol 310 thereon, e.g., printed thereon, formed therein as a depression (as in the illustrated embodiment), formed thereon as a protrusion, embedded therein, etc. The symbol 310 can include any one or more of numbers, alphabet characters, and geometric shapes, logos, and other symbols. Although only one symbol 310 is shown in the illustrated embodiment, a housing can include any number of symbols thereon. The symbol 310 can identify a manufacturer of the accessory 12, can identify a specific consumable or type of consumables for use with the accessory 12, and/or can be decorative (e.g., a person's name, a person's first initial, a cartoon character, etc.). In the illustrated embodiment, the symbol 310 includes a plus sign. Symbols for accessories are further described in previously mentioned Intl. App. No. PCT/US13/047507.

Figure 7:
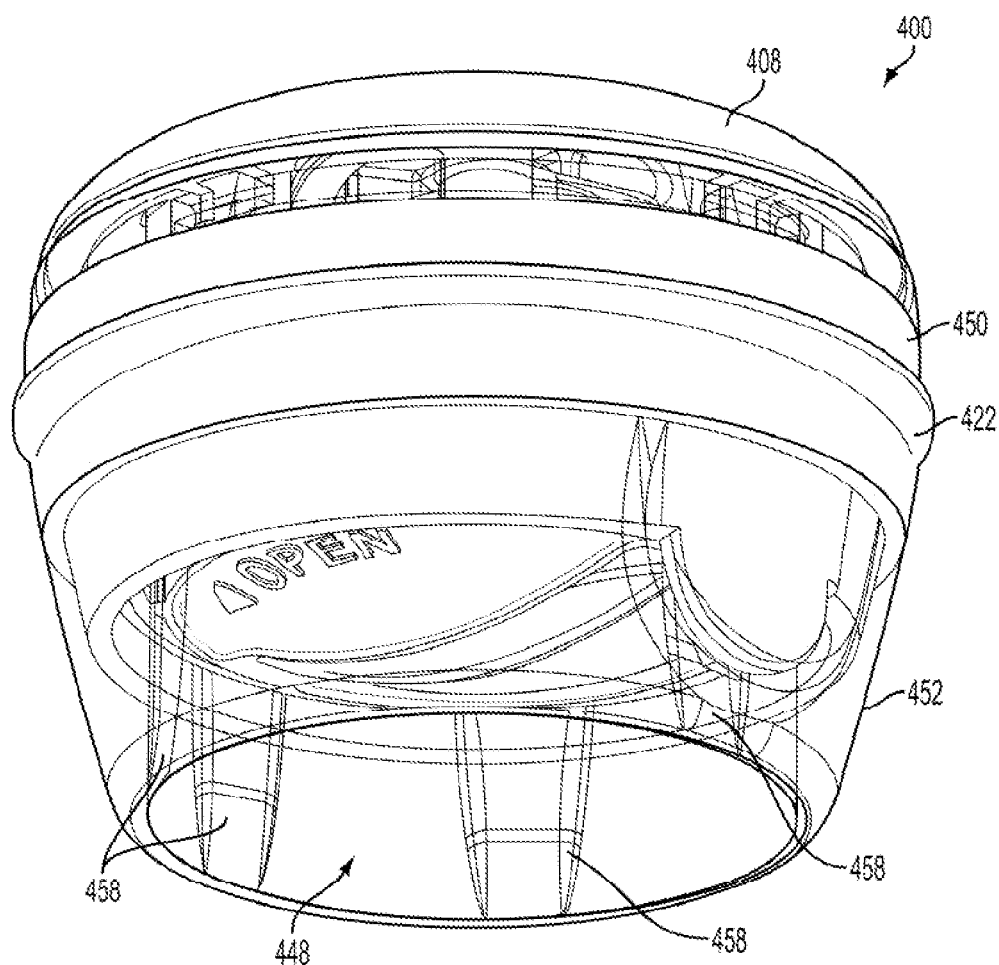
FIG. 7 is a perspective partially transparent view of one embodiment of an accessory configured to be removably and replaceably attached to a consumables dispenser.
Figure 8:
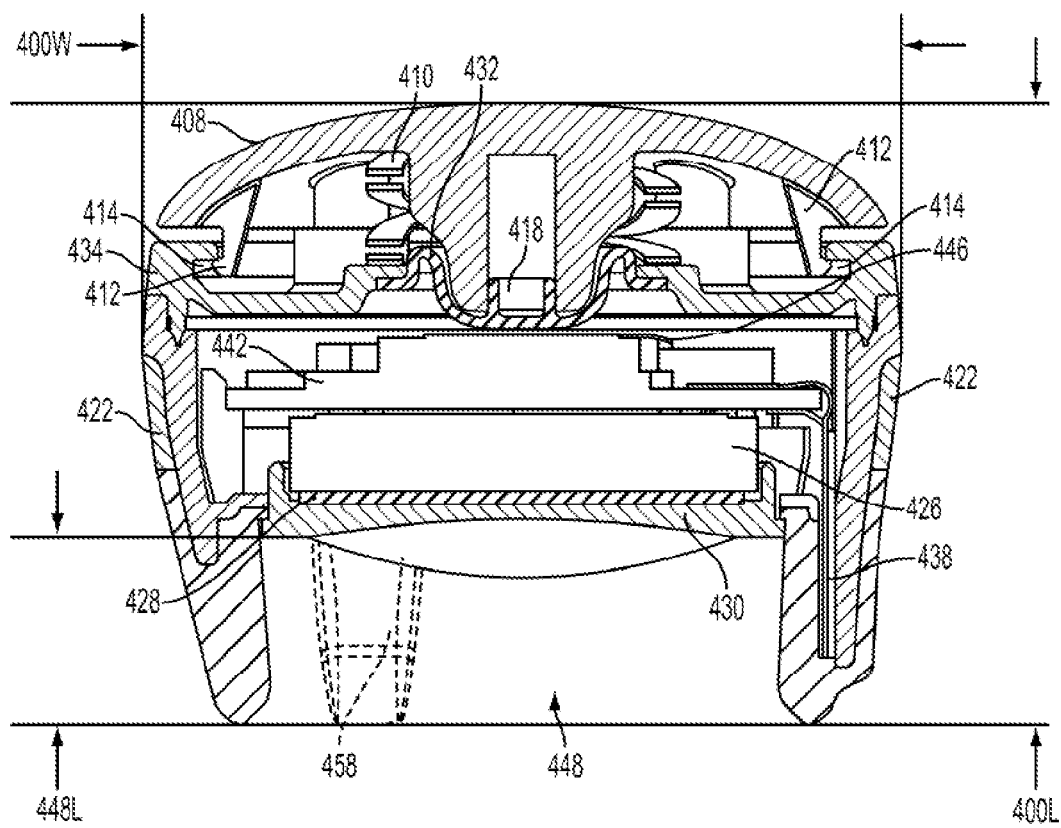
FIG. 8 is a side cross-sectional view of the accessory of FIG. 7.
Figure 9:
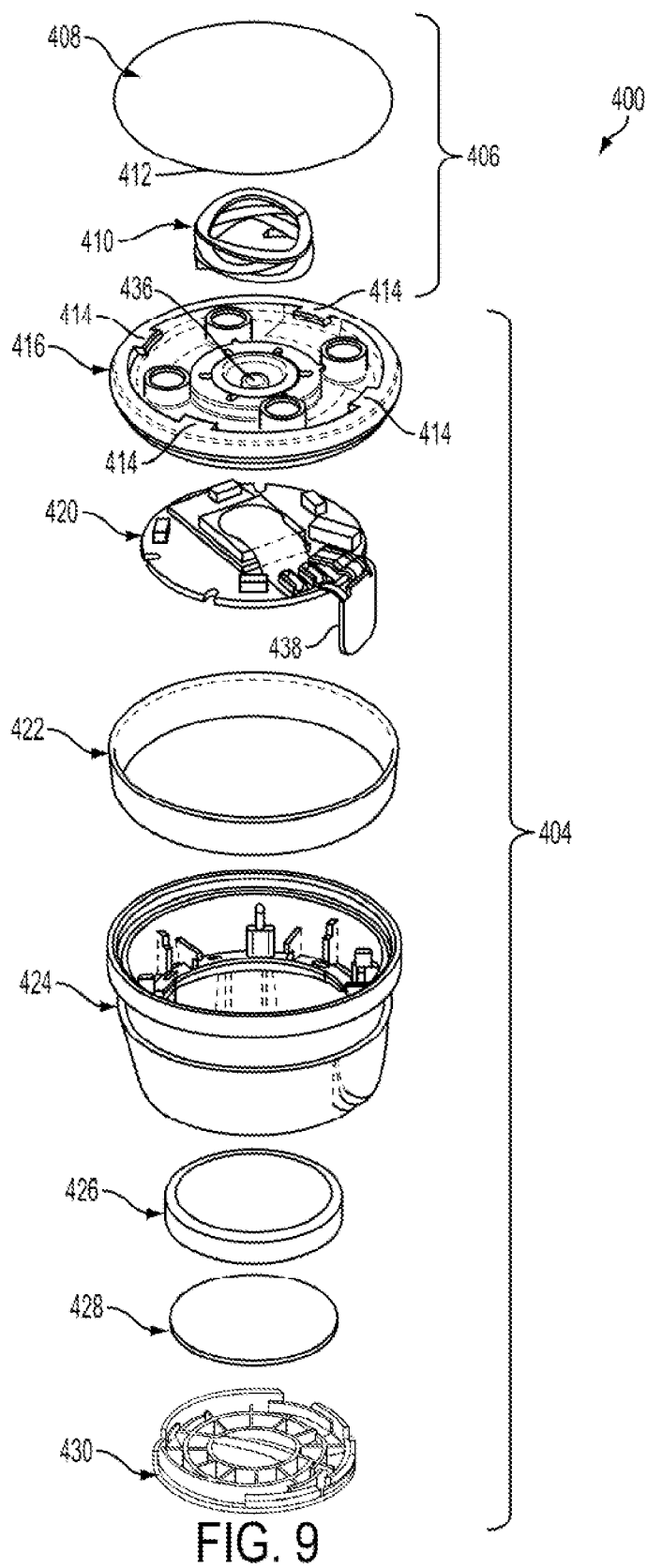
FIG. 9 is an exploded perspective view of the accessory of FIG. 7.
Figure 10:
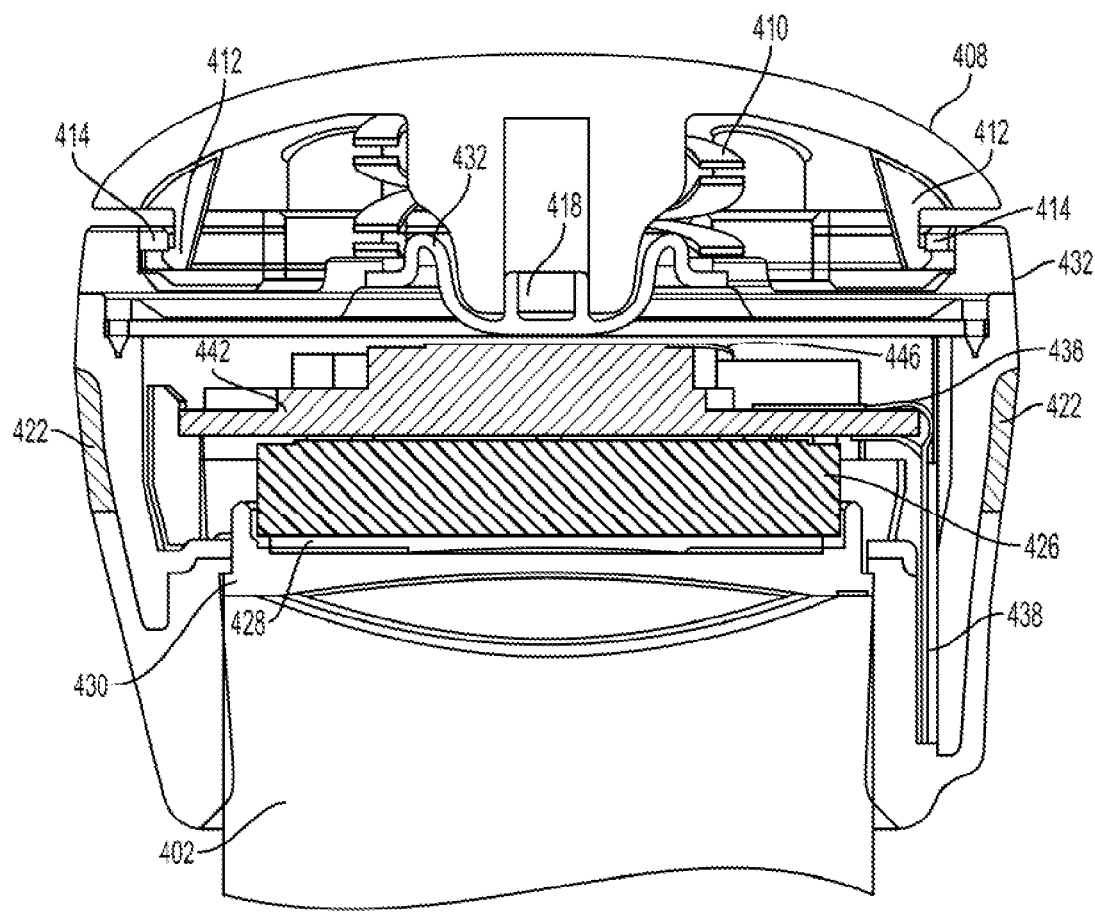
FIG. 10 is side cross-sectional view of the accessory of FIG. 7, the accessory removably and replaceably attached to a consumables dispenser.

FIGS. 7-10 illustrate another embodiment of an accessory 400 in the form of a cap configured to be removably and replaceably attached to a dispenser. The accessory 400 is shown in FIGS. 7-9 as a standalone element unattached to any dispenser and is shown in FIG. 10 removably and replaceably attached to a canister 402 of a consumables dispenser. The canister 402 in this illustrated embodiment contains an inhalable consumable, e.g., respiratory medication, disposed therein, and is configured to be seated in a housing (not shown) and moved relative thereto to dispense the consumable through a mouthpiece (not shown) of the dispenser housing, as discussed herein. However, as mentioned above, the accessory 400 can be configured to attach to a variety of different types of dispensers containing different types of consumables.

As in this illustrated embodiment, the accessory 400 can include a distal portion 404, also referred to herein as a "distal base," and a proximal portion 406, also referred to herein as a "proximal cap." The proximal cap 406 can be configured to move relative to the distal base 404, thereby causing the consumable to be dispensed from the dispenser and causing the accessory 400 to detect usage of the dispenser, e.g., to detect that the consumable was dispensed. The proximal cap 406 and the distal portion 404 can each have a variety of sizes, shapes, and configurations.

As in this illustrated embodiment, the proximal cap 406 can include a lid 408 and a bias element 410. The lid 408 can have a variety of sizes, shapes, and configurations. In this illustrated embodiment, the lid 408 includes a domed member. The lid 408 can include a mating element 412 configured to engage a corresponding mating feature 414 of the distal base 404 so as to non-removably mate the proximal cap 406 to the distal base 404. Such permanent fixation of the proximal and distal portions 406, 404 can help protect any electronic components disposed within the accessory 400. In some embodiments, the proximal cap 404 can be removably and replaceably mated to the distal base 404, which can allow replacement of one or more the accessory's electronic components, e.g., replacement of a depleted battery, replacement of a burned out light, etc.

Figure 11:
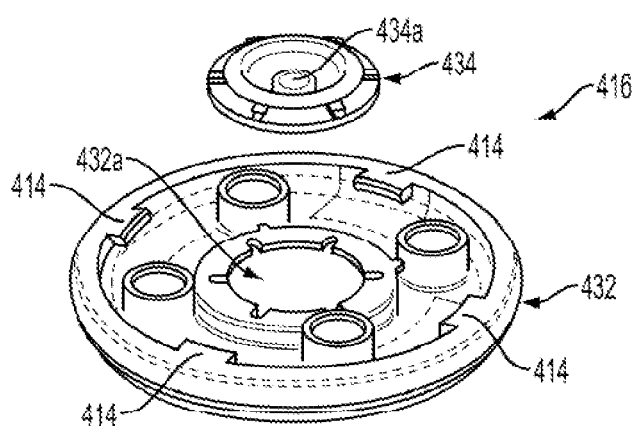
FIG. 11 is an exploded perspective view of a spin ring of the accessory of FIG. 10.

As in this illustrated embodiment, the mating element 412 can include a bayonet foot extending distally from the proximal cap 406, and the mating feature 414 can include a ledge extending from the distal base 404, e.g., from a spin ring 416 of the distal base 404. The spin ring 416 is also illustrated in FIG. 11. The ledge in this illustrated embodiment includes four ledges extending radially inward from an interior surface of the distal base 404, one ledge for each bayonet foot. In other embodiments, there can be another number of ledges and another number of bayonet feet. For example, there can be one ledge configured to engage each bayonet foot, e.g., one ledge extending circumferentially around the spin ring 416. For another example, there can be an equal number of bayonet feet and ledges such that each one of the bayonet feet engages one of the ledges. The bayonet foot can be configured to be movable toward and away from the ledge in response to the proximal cap 406 being depressed, e.g., by a user manually pressing down on the lid 408, and released, e.g., by the user releasing manual pressure from the lid 408. In other embodiments, the distal base's mating feature can include a bayonet foot, and the proximal cap's mating element can include a ledge.

The lid 408 can include a button 418 facing the distal base 404. In general, the button 418 can be configured to be depressed when a consumable is dispensed from a dispenser to which the accessory 400 is attached, e.g., from the canister 402 of FIG. 10, as discussed further below. The button 418 can thus be configured to detect usage of the dispenser.

The lid 408 can be configured to be movable relative to the distal base 404 between a first position and a second position. In the first position, the lid 408 can be at a first distance from the distal base 404, the at least one mating element 412 can be engaged with the at least one mating feature 414 (e.g., the bayonet feet can be in contact with the ledges, as shown in FIGS. 8 and 10), the bias element 410 can be in an expanded configuration, and the button 418 can be out of contact from the distal base 404. In the second position, the lid 408 can be at a second distance from the distal base 404 that is less than the first distance, the at least one mating element 412 can be disengaged from the at least one mating feature 414 (e.g., the bayonet feet can be out of contact with the ledges), the bias element 410 can be in a compressed configuration, and the button 418 can be pressed against the distal base 404 (e.g., against a processor assembly 420 of the distal base 404, discussed further below). The first distance can define a void space between the button 418 and the distal base 404 (e.g., against the processor assembly) when the button 418 is in a non-depressed position, as in FIGS. 8 and 10. The void space can provide some "give" space for movement of the button 418, which can help prevent the consumable from being accidentally dispensed.

The bias element 410 can have a variety of sizes, shapes, and configurations. In general, the bias element 410 can be configured to bias the lid 408 to the first position, e.g., bias the button 418 away from the processor assembly 420. Examples of the bias element 410 include a coil spring, a volute spring, an elastic member similar to a rubber band, a leaf spring, and a wave spring. In this illustrated embodiment, the bias element 410 includes a wave spring. A bias strength or spring rate of the bias element 410 can vary based on one or more factors, such as a height of the bayonet feet 412, a height of the button 418, etc. For example, the bias strength or spring rate of the bias element 419 can be about 26.0 lb/in. A size of the bias element 410 can vary based on one or more factors, e.g., a diameter of the button 418, a diameter of the lid 408, etc. For example, the bias element 410 can have an outer diameter of about 0.526 in., a radial wall thickness of about 0.058 in., and a free length of about 0.325 in. A person skilled in the art will appreciate that a bias element may not have a precise measurement but nevertheless be considered to be "about" that measurement due to one or more factors, such as manufacturing tolerances.

In an exemplary embodiment, the bias element 410 can surround the button 418, e.g., extend circumferentially therearound, as in this illustrated embodiment. By extending circumferentially around the button 418 configured to be pressed in response to manual actuation of the accessory 400 by a user, e.g., by the user pressing down thereon, the bias element 410 can be configured to help evenly transmit the force applied by the user to the button 418, thereby helping to ensure that the button 418 is pressed against the distal base 404 regardless of where on the lid 408 the user presses to dispense a consumable. For example, if a user presses down on the lid 408 at a substantial center thereof (e.g., where a symbol is on the lid 408) so as to be pushing substantially directly on top of the button 418, the applied user force can facilitate pressing of the button 418. However, a user may not always press the lid 408 at a substantial center thereof and/or may not always press on the lid 408 in a direction that the button 418 extends such that the button 418 is not pressed directly downward. The bias element 410 completely surrounding the button 418, as in this illustrated embodiment, can help ensure that off-center user pressure on the lid 408 presses the button 408 down against the distal base 404. The bias element's center can be substantially at the button's center, as in this illustrated embodiment, which can help ensure that off-center user pressure on the lid 408 presses the button 408 down against the distal base 404, even if the pressure is far off the lid's center.

Figure 12:
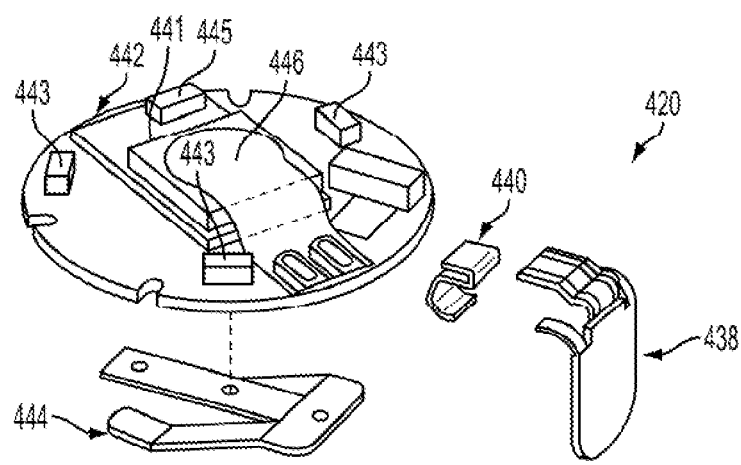
FIG. 12 is an exploded perspective view of a printed circuit board of the accessory of FIG. 10.
Figure 13:
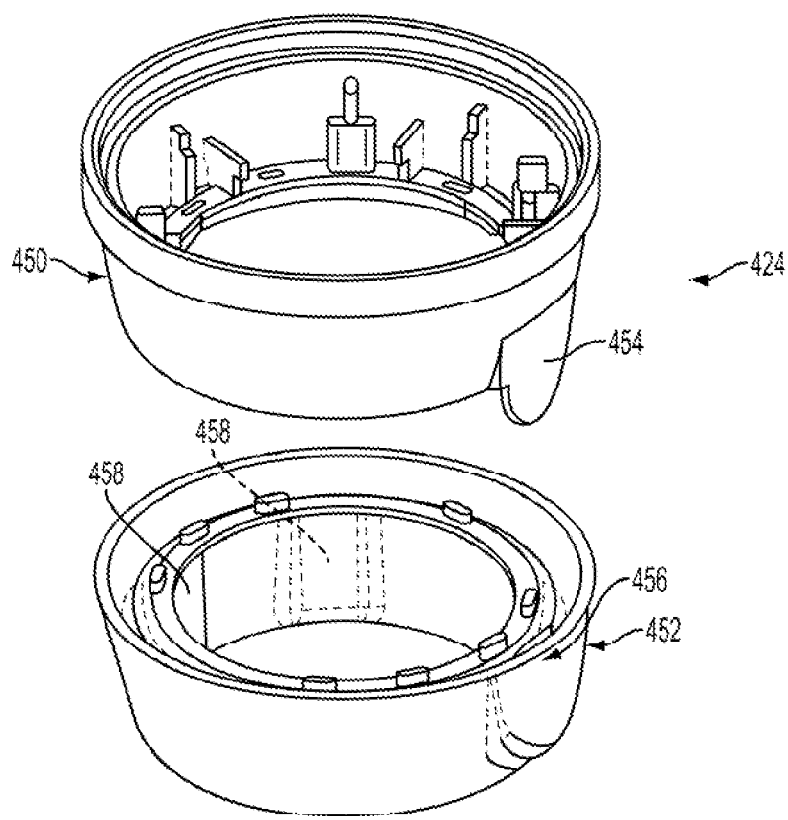
FIG. 13 is an exploded perspective view of a main body of the accessory of FIG. 10.

As in this illustrated embodiment, the distal base 404 can include the spin ring 416, the processor assembly 420 (also shown in FIG. 12), a grip ring 422, a main body 424 (also shown in FIG. 13), a power source 426, a power source protective member 428, and a power source housing 430. The spin ring 416, the processor assembly 420, the grip ring 422, the main body 424, the power source 426, the power source protective member 428, and the power source housing 430 can each have a variety of sizes, shapes, and configurations.

The spin ring 416 can include an outer member 432 and an inner member 434 configured to be seated in the outer member 432, e.g., seated in a central portion thereof. The outer and inner members 432, 434 can be overmolded. The spin ring 416, e.g., the outer member 432, can be configured to seat the bias element 410 so as to sandwich the bias element 410 between the spin ring 416 and the lid 408. The spin ring 416 can have a central opening 436 extending therethrough in which the button 418 can be configured to move in a downward direction toward the processor assembly 420 underlying the spin ring 416 and to move in an upward direction away from the processor assembly 420. Each of the outer and inner members 432, 434 can have central apertures 432a, 434a that define the central opening 436.

The processor assembly 420 can include a side sensor 438, a positive power source contact 440, a processor 441, a PCB 442, at least one light 443 (e.g., at least one LED, etc.), a negative power source contact 444, an antenna 445 configured to facilitate wireless communication, and a force sensitive resistor 446. The processor 441 can include a memory (not shown). The positive and negative power source contacts 440, 444 can be configured to contact corresponding positive and negative contacts of the power source 426 to facilitate power supply from the power source 426 o the PCB 442.

The PCB 442 can, as mentioned above, be coupled to the accessory's processor, or the PCB 442 can be configured to cooperate with at least one off-board component, e.g., a CPU control store (CCS) module located outside the accessory 400. As discussed above, the PCB 442 can be configured to, in response to actuation of the button 418 on the force sensitive resistor 446 (e.g., by moving the proximal portion 406 toward to the distal portion 404), record the date and time of the usage of the dispenser to which the accessory 400 is coupled in a storage unit, such as an on-board memory included in the PCB 442. The stored data can be transmitted to an external source, e.g., computer system, as also discussed above.

The force sensitive resistor 446 can be configured to facilitate detection of the movement of the proximal cap 406 relative to the distal base 404 so as to facilitate detection of a consumable being dispensed from a dispenser to which the accessory 400 is attached. In general, the force sensitive resistor 446 can be configured as a pressure sensor that senses a weight or pressure being exerted thereon. The force sensitive resistor 446 can be configured to change resistance when pressure is applied thereto, as will be appreciated by a person skilled in the art. The button 418 can be configured to move within the central opening 436 of the spin ring 416 and can be configured to contact the force sensitive resistor 446 underlying the spin ring 416 when moved in a downward direction toward the PCB 442 and hence toward the force sensitive resistor 446. The force sensitive resistor 446 can be configured to change resistance in response to pressure applied thereto from the button 418. In this way, when the lid 408 is pressed downward so as to move the button 418 in a downward direction, the button 418 can apply pressure to the force sensitive resistor 446, thereby changing the force sensitive resistor's resistance to indicate actuation of the cap 400 and dispensing of a consumable. Similarly, when the lid 408 is released so as to move upwardly, the button 408 can move upwardly so as to decrease pressure on the force sensitive resistor 446, thereby again changing the resistance of the force sensitive resistor 446.

The processor can be configured to compare the force sensitive resistor's resistance value with a predetermined threshold resistance value, e.g., a value stored in the memory, so as to determine whether the consumable has been dispensed. The resistance value can be a numerical value of the actual resistance or can be a value representative of the actual resistance. By being able to compare specific values instead of merely detecting a sensor's "on" or "off" position, e.g., "on" as having pressure applied thereto and "off" as having no pressure applied thereto, to determine dispensing of the consumable, the processor can help eliminate false positives. If the force sensitive resistor's resistance value equals or exceeds the threshold resistance, then the processor can be configured to determine that the consumable was dispensed because a certain threshold amount of pressure has been applied to the accessory 400 attached to the dispenser containing the consumable. For example, if the threshold resistance value corresponds to a pressure of 20 N, but the force sensitive resistor's resistance value corresponds to a pressure of 15 N (e.g., increases from 0 N without any contact with the button 418 to 15 N upon contact with the button 418), then the processor can determine that dispensing of the consumable did not occur. In other words, the lid 408 can be presumed to have not been pushed with enough force to cause the consumable to exit the canister 402. For another example, if the threshold resistance value corresponds to a pressure of 25 N and the force sensitive resistor's resistance value corresponds to a pressure of 26 N (e.g., increases from 0 N without any contact with the button 418 to 26 N upon contact with the button 418), then the processor can determine that actuation did occur. In other words, the lid 408 can be presumed to have been pushed with enough force to cause the consumable to exit the canister 402.

The predetermined threshold resistance value can depend on the dispenser to which the accessory is attached, e.g., different canisters can require different amounts of force to dispense a consumable therefrom. The memory can be configured to store threshold resistance values for various canisters, and the processor can be configured to compare the force sensitive resistor's resistance value with the one of the threshold resistance values corresponding to the canister to which the accessory 400 is coupled. In some embodiments, the threshold resistance value for the canister to which the accessory 400 is attached can be transmitted to the PCB 442 using the wireless bridge, and the transmitted threshold resistance value can be stored in the memory for later comparison with resistance values of the force sensitive resistor 446. The correct threshold resistance value for the processor to compare with the force sensitive resistor's resistance value can be determined, whether the threshold resistance value is pre-stored in the memory or is transmitted to the accessory 400, by having identification information transmitted thereto. Transmission of identification information, as well as other types of data, to an accessory is described in further detail in previously mentioned Intl. App. No. PCT/US13/047507.

In an exemplary embodiment, a user can enter consumable schedule information (e.g., prescription information for the consumable with which the accessory 400 will be used, meal times when a vitamin with which the accessory 400 will be used should be consumed, etc.) and consumable identification information (e.g., identification of the specific consumable with which the accessory 400 will be used, the specific supplement with which the accessory 400 will be used, etc.) via a user interface via a client terminal, as discussed herein. The user interface can be configured to provide a list of consumables from which the user can select to identify the specific consumable, and/or the user interface can allow the user to enter any consumable. The client terminal can be configured to have access to a database of consumables and their associated threshold resistance values, with the database being stored locally at the client terminal or remotely accessible to the client terminal. The client terminal can be configured to determine from the database which threshold resistance value corresponds to the consumable identified by the user. The client terminal can be configured to communicate with the accessory 400, e.g., via wireless communication between the accessory 400 and, to provide the consumable schedule information, the consumable identification information, and the threshold resistance value to the accessory 400, which can store the received data in the memory. The accessory 400 can thus be configured to compare the force sensitive resistor's resistance value with the threshold resistance value appropriate for the specific dispenser to which the accessory 400 is coupled.

The side sensor 438 can be configured to facilitate detection of the accessory's attachment to and removal from a consumables dispenser. Detecting whether the accessory 400 is attached to a dispenser can facilitate proper attachment of the accessory 400 to the dispenser and/or facilitate proper use of the accessory 400. As in this illustrated embodiment, the accessory 400 can itself be configured to determine accessory removal/attachment, e.g., using the side sensor 438 and the PCB 420. In other embodiments, a processor that is off-board the accessory 400 can be configured to detect removal and attachment of the accessory 400 with respect to a consumables dispenser.

The side sensor 438 can be located adjacent a perimeter of the accessory 400 so as to be located at a radial outward location. The side sensor 438 can be configured to sense pressure. When a dispenser, e.g., a medicament canister such as the canister 402, is seated in a cavity 448 of the accessory 400, e.g., of the main body 424, the dispenser can exert outward pressure on the accessory 400 so as to apply pressure to the side sensor 438. The side sensor 438 can be configured to sense this pressure directed radially outward, thereby allowing the processor to determine that a dispenser has been attached to the accessory 400 since the side sensor 438 sensed an increase in pressure. Similarly, when a dispenser is removed from the cavity 448, the pressure exerted on the side sensor 438 can decrease. The processor can accordingly determine that the accessory 400 is no longer coupled to the dispenser since the side sensor 438 sensed a decrease in pressure.

The side sensor 438 can facilitate the accessory 400 moving from a first mode, in which the accessory 400 is inactive as not being attached to a dispenser, to a second mode, in which the accessory 400 is active as being attached to a dispenser. In the first mode, the accessory 400 can be configured to use no or little power from the power source 426, thereby conserving resources. In some embodiments, the accessory 400 can have a third mode in which the accessory 400 is inactive as not being attached to a dispenser and as never having been attached to a dispenser. The third mode can thus reflect that the accessory 400 is at a manufacturing plant and/or is in factory packaging so as to be "new." The accessory 400 in the third mode can be configured to use no power and to not communicate with an external device wirelessly or via wire. The third mode can thus be the accessory's initial mode. Once the accessory 400 has been attached to a dispenser at least once, the accessory 400 can be configured to move between the first and second modes. In the first mode in which the accessory 400 is inactive, as compared to the third mode in which the accessory 400 is also inactive, the accessory 400 can be configured to use a low amount of power so as to allow an external device to communicate with the accessory 400, e.g., to receive data stored in the accessory's memory regarding the accessory's previous attachment to a dispenser such as a date and time the accessory 400 was last removed from a dispenser, etc. By allowing the external device to communicate with the accessory 400 when the accessory 400 is not currently attached to a dispenser but was so attached in the past, the external device can be more likely to have the most up to date information and/or can use date and time information regarding the accessory's removal from the dispenser to prompt the user to indicate via the user interface why the accessory 400 was removed from the dispenser (e.g., accidental removal, change in prescription, change of accessory owner, broken accessory, broken dispenser, etc.).

The accessory 400 can be configured to provide a notification to a user of the accessory 400 regarding the accessory's attachment and/or the accessory's non-attachment to the dispenser. The PCB 420 can be configured to trigger the notification in response to the detection of the attachment and/or detection of the removal. The notification can be provided in any one or more ways, such as a light (e.g., a light that illuminates when the accessory 400 is not attached to a dispenser and is otherwise unilluminated, a light that blinks when the accessory 400 is not attached to a dispenser and is otherwise unilluminated, a light that illuminates in one color when the accessory 400 is not attached to a dispenser and a second light that illuminates in a different color when the accessory 400 is not attached to a dispenser, etc.); a vibration element (e.g., a vibration element that vibrates for a predetermined length of time upon the accessory 400 being attached to a dispenser and is otherwise non-vibrating, a vibration element that vibrates for a predetermined length of time in response to the accessory 400 being unattached to a dispenser and is otherwise non-vibrating, a vibration element that in response to the accessory 400 being unattached to a dispenser alternatively vibrates for a predetermined length of time and does not vibrate for a predetermined length of time, etc.); and an email message, a text message, an icon alert (e.g., a pop-up text and/or image on a smartphone or computer, etc.) or a phone call (which can be a live phone call or an automated phone call and can include leaving a voicemail or other recorded message) being sent to a location remote from the dispenser, etc.

The notification can prompt the user for an action, such as confirming (e.g., via a user interface) whether the accessory 400 was replaced on the same dispenser that it was previously coupled to or was coupled to a different dispenser. Being placed onto the same or different dispenser can be important, for example, for dose scheduling purposes since a different dispenser may be associated with a different schedule, e.g., as being associated with a different prescription, as being a stronger or weaker concentration of medicine, etc. Another example of the action includes confirming to the user that the accessory 400 was properly attached to the dispenser and is therefore ready to use. Another example of the action includes informing a user when the dispenser does not have the accessory 400 attached thereto, thereby indicating to the user that the dispenser should have the accessory 400 and/or other accessory attached thereto before dispensing any consumable therefrom. All consumable usage can therefore be more likely to be detected and analyzed.

In other embodiments, in alternative to or in addition to a side sensor such as the side sensor 438, an accessory can be configured to identify removal/reattachment to/from a dispenser by opening an electrical circuit when the accessory is removed and by closing the electrical circuit when the accessory is replaced. The accessory can thus be configured to indicate whether it is attached to a dispenser or not attached to a dispenser. The accessory can be configured to make this determination itself, e.g., using an on-board processor configured to identify removal/reattachment of the accessory such as by detecting whether the electrical circuit is open or closed. Alternatively or additionally, a processor that is off-board from the accessory can be configured to identify such removal/reattachment.

In some embodiments, in alternative to or in addition to a side sensor such as the side sensor 438, an accessory can be configured to identify removal/reattachment to/from a dispenser using a stretch sensor configured to change an electrical property (e.g., resistance) in response to being stretched. When the stretch sensor is stretched, the changed electrical property can indicate that that accessory to which the stretch sensor is coupled has been coupled to or removed from a consumables dispenser. For example, an accessory configured to couple to a cap of a pill bottle can include a stretch sensor configured to stretch when the cap is attached to or removed from the pill bottle.

The grip ring 422 can be configured to facilitate handling of the accessory 400. The grip ring 422 can be formed from rubber and/or other material configured to facilitate gripping of the accessory 400 by hand. The grip ring 422 can be particularly useful in gripping the accessory 400 during attachment of the accessory 400 to and removal of the accessory 400 from a dispenser. The grip ring 422 can be of a color different than a color of the main body 424, e.g., a primary color grip ring 422 and a white main body 424, etc., which can help improve aesthetics of the accessory 400 and/or can help facilitate identification of the dispenser to which the accessory 400 is attached, e.g., an accessory with a yellow grip ring being attached to a person's regular inhaler and another accessory with a red grip ring being attached to the person's emergency inhaler. In some embodiments, the main body 424 can be color-coded in a similar way, e.g., different colored main bodies being attached to different consumable containers.

The main body 424 can include a proximal body 450 and a distal body 452. In an exemplary embodiment, the proximal and distal bodies 450, 452 can be non-removably attached together in a fluid tight seal, which can help protect the components contained within the main body 424 and/or can help prevent fluid from leaking into the accessory 400 and damaging any components disposed therein. The proximal and distal bodies 450, 452 can be overmolded to form the main body 424 and be non-removably attached together. The proximal portion's lid 408 and the distal portion's main body 424 can define a housing of the accessory 400 which, as discussed above, can have some degree of flexibility (e.g., the deformation of the distal body 452), can be transparent or translucent (e.g., at least the lid 408 through which a light can be configured to glow), can be waterproof, can be permanently closed or sealed, and/or can be configured to be disposable.

The proximal body 450 can include a sensor protector 454 extending distally therefrom at a sidewall thereof, e.g., at a perimeter of the proximal body 450. The sensor protector 454 can be configured to have the side sensor 438 disposed adjacent thereto, and the sensor protector 454 can be configured to protect the side sensor 438 so positioned and/or be configured to facilitate electronic communication between the side sensor 438 and the PCB 442. The distal body 452 can include a pocket 456 formed in a sidewall thereof and configured to receive the sensor protector 454 and the side sensor 438 therein. The pocket 456 can help protect the side sensor 438 from pressure applied thereto, e.g., pressure directed radially outward from a dispenser inserted into the cavity 448.

The main body 424 can define the accessory's cavity 448 configured to receive a dispenser, e.g., a canister such as the canister 402, in a distal portion thereof. The main body 424 can be configured to deform in response to insertion of the dispenser into the cavity 448. The cavity's sidewall can be defined by an inner surface of the distal body 452, as in this illustrated embodiment. The distal body 452 can be formed from a material (e.g., thermoplastic elastomers, etc.) configured to flex so as to allow the deformation. The proximal body 450 can be formed from a material (e.g., ABS, etc.) that is more rigid than the material forming the distal body 452, which can help provide stability to the main body 424 and the accessory 400 while still allowing the accessory 400, e.g., the distal body 452, to deform in response to the accessory 400 being coupled to a dispenser. The deformation of the accessory 400, e.g., of the main body's distal body 452, can facilitate a secure interference fit between the accessory 400 and the dispenser to which the accessory 400 is coupled. Different dispensers can have different sizes, and the deformation can make the accessory 400 more versatile by facilitating a secure interference fit between the accessory 400 and different sized dispensers.

The main body 424 can include a grip mechanism 458 which, as mentioned above, can be configured to facilitate attachment of the accessory 400 to a dispenser and can be configured to deform when the accessory 400 is attached to a dispenser. As in this illustrated embodiment, the grip mechanism 458 can include a plurality of protrusions extending radially inward from the cavity 448, e.g., from the inner surface of the distal body 452 that defines the cavity 448. Although the accessory 400 includes four grip mechanisms 458 in this illustrated embodiment, an accessory can include another number of grip mechanisms. Each of the grip mechanisms 458 can be configured to deform radially outward in response to pressure exerted thereon by a dispenser inserted into the cavity 448. In this illustrated embodiment, the protrusions each include a longitudinally extending rib that extends along an entire longitudinal length 448L of the cavity 448, as shown in FIG. 8. In this illustrated embodiment, the cavity's longitudinal length 448L of the cavity 448 is about 0.32 in., but the longitudinal length 448L of the cavity 448 can be different in other embodiments. Similarly, the accessory's longitudinal length 400L is about 1.04 in. and the accessory's width 400W is about 1.28 in. in this illustrated embodiment, but the accessory 400 in other embodiments can have a different longitudinal length 400L and/or a different width 400W. The values of the accessory's longitudinal length 400L and width 400W in this illustrated embodiment can facilitate use of the accessory 400 with a variety of currently available respiratory inhalers.

The power source 426 can be configured to provide power to one or more components of the accessory 400, e.g., components of the PCB 420. The processor 441 can be configured to facilitate power saving by being configured to move between a first state in which the power source 426 provides a first amount of power to components of the accessory 400 and a second state in which the power source 426 provides a second, greater amount of power to the components of the accessory 400. The power source 426 is in the form of a coin cell battery in this illustrated embodiment, and is only a single battery, but the power source in other embodiments can be another type of power source (e.g., another type of battery, etc.) and/or can include more than one power source (e.g., include a battery pack, etc.).

The power source protective member 428 can be configured to help protect the power source 426 from being damaged during movement of the accessory 400 when a consumable is being dispensed. The power source protective member 428 can have a size and shape corresponding to a size and shape of the power source 426, which can facilitate full protection of the power source. The power source protective member 428 in this illustrated embodiment includes a cushion, but the power source protective member 428 can have other configurations in other embodiments.

The power source housing 430 can be configured to seat the power source protective member 428 and the power source 426 therein. The power source housing 430 can be permanently closed so as to prevent access to the power source 426 seated therein or, as in this illustrated embodiment, the power source housing 430 can be configured to be selectively closed so as to allow access to the power source 426 seated therein. Allowing access to the power source 426 can allow the power source 426 to be removed and replaced in the event that the power source 426 is depleted and/or allow the power source 426 to be removed for safety reasons prior to disposal of the accessory 400. The power source housing 430 can be configured to be selectively closed in a variety of ways. For example, as in this illustrated embodiment, the power source housing 430 can be configured to be detached from and reattached to the main body 424, such as by being twisted. For another example, the power source housing 430 can include a hinged door (not shown) configured to allow the power source housing 430 to be selectively manually opened and closed.

An accessory can be configured to be attached to a consumables dispenser in a variety of different locations relative to the dispenser. In some embodiments, an accessory can be configured to be attached to a top of a consumables dispenser. For example, the accessory can be configured to attach to a top of a canister of a dispenser, such as a canister containing respiratory medication and being configured to be seated in a housing of the dispenser, e.g., an exterior plastic container of a respiratory inhaler (e.g., an asthma inhaler). The accessory 302 of the embodiment of FIG. 4, the accessory 400 of the embodiment of FIG. 7, and accessories 600, 700, 800, 900, 1000, 1100, 1200, and 1300, of the embodiments of FIGS. 14-21 are examples of accessories configured to be attached to a top of a dispenser. The specific locations where accessories are attached to dispensers in the illustrated embodiments of FIGS. 14-21 as well as in other embodiments provided herein are examples, and accessories can be attached at various other locations, e.g., a different location on an external surface of a dispenser.

Figure 14:
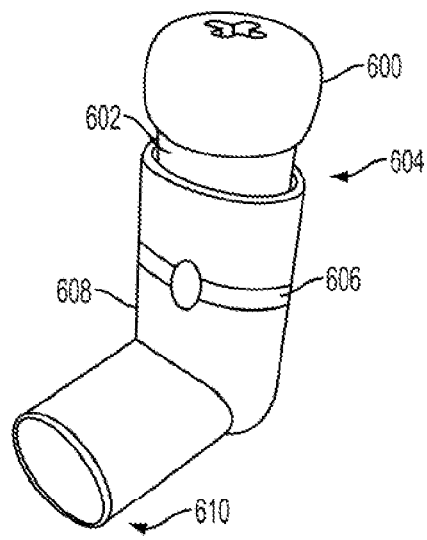
FIG. 14 is a perspective view of one embodiment of a consumables dispenser in the form of a respiratory inhaler having first and second accessories attached thereto.

The accessory 600 of FIG. 14 is a cap similar to the accessory 302 of FIG. 4 and is shown in FIG. 14 coupled to a top of a canister 602 of a consumable dispenser 604 in the form of a respiratory inhaler similar to the dispenser 304 of FIG. 4. The dispenser 604 in this illustrated embodiment also has a second accessory 606 coupled thereto. The second accessory 606 in this illustrated embodiment includes a band or strap configured to be wrapped around the dispenser 604, e.g., around a housing 608 thereof that seats the canister 602 therein and that is configured to be held by hand when the consumable is dispensed through the dispenser's mouthpiece 610. The second accessory 606 in this illustrated embodiment includes a sensor in the form of a motion sensor.

Figure 15:
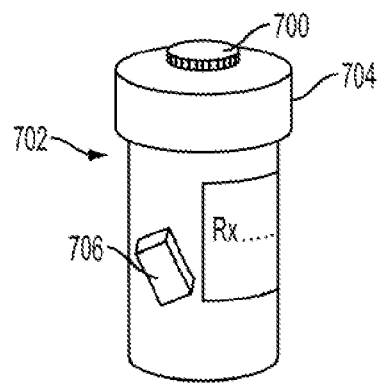
FIG. 15 is a perspective view of one embodiment of a consumables dispenser in the form of a pill bottle having first and second accessories attached thereto.

In the embodiment of FIG. 15, the accessory 700 is coupled to a consumables dispenser 702 in the form of a pill bottle having a releasable cap 704 at a top thereof to which the accessory 700 is coupled. The accessory 700 can include a motion sensor. The dispenser 702 in this illustrated embodiment also has a second accessory 706 coupled thereto, which can include a second motion sensor. The second accessory 706 in this illustrated embodiment is disposed inside the dispenser 702 where the pills are contained. The second accessory 706 can be freely movable within the dispenser 702 similar to a pill being freely movable therein, as in this illustrated embodiment, which can facilitate removing and replacing the second accessory 706. Alternatively, the second accessory can be coupled to an inner surface of the dispenser 702, e.g., to an interior sidewall thereof, such as with an adhesive.

Figure 16:
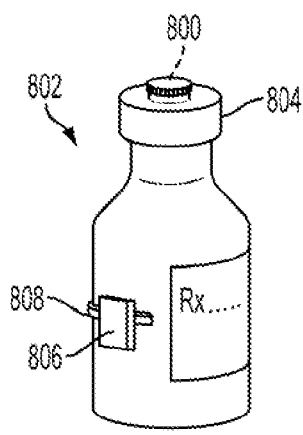
FIG. 16 is a perspective view of another embodiment of a consumables dispenser in the form of a pill bottle having first and second accessories attached thereto.

In the embodiment of FIG. 16, the accessory 800 is coupled to a consumables dispenser 802 in the form of a pill bottle having a releasable cap 804 at a top thereof to which the accessory 800 is coupled. The dispenser 802 in this illustrated embodiment also has a second accessory 806 coupled thereto Similar to the embodiment of FIG. 15, the two accessories 800, 806 can each include a motion sensor. The second accessory 806 in this illustrated embodiment is coupled to an exterior surface of the dispenser 802. The second accessory 806 can be attached to the dispenser's exterior surface in a variety of ways, such as by using a Velcro® strap 808 (as in this illustrated embodiment), an adhesive, etc.

Figure 17:
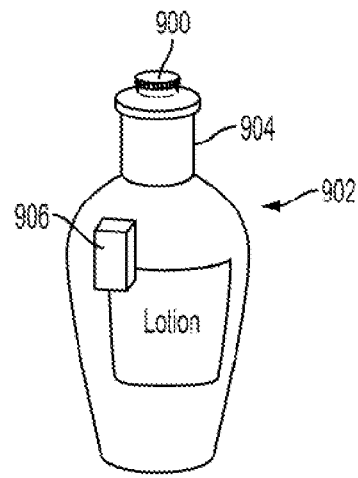
FIG. 17 is a perspective view of one embodiment of a consumables dispenser in the form of a lotion bottle having first and second accessories attached thereto.

In the embodiment of FIG. 17, the accessory 900 is coupled to a consumables dispenser 902 in the form of a lotion bottle having a releasable cap 904 at a top thereof to which the accessory 900 is coupled. The dispenser 902 in this illustrated embodiment also has a second accessory 906 coupled thereto. Similar to the embodiment of FIG. 15, the two accessories 900, 906 can each include a motion sensor Similar to the embodiment of FIG. 16, the second accessory 906 can be coupled to an exterior surface of the dispenser 902.

Figure 18:
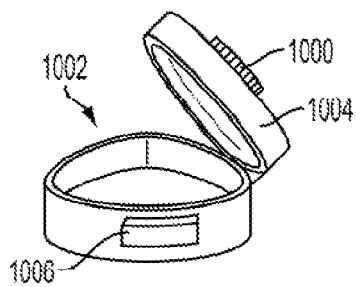
FIG. 18 is a perspective view of one embodiment of a consumables dispenser in the form of a pill box having first and second accessories attached thereto.

In the embodiment of FIG. 18, the accessory 1000 is coupled to a consumables dispenser 1002 in the form of a pill box having a releasable cap 1004 at a top thereof to which the accessory 1000 is coupled. The releasable cap 1004 in this illustrated embodiment is hinged, but as will be appreciated by a person skilled in the art, pill boxes in other embodiments can have other types of releasable caps The dispenser 1002 in this illustrated embodiment also has a second accessory 1006 coupled thereto Similar to the embodiment of FIG. 15, the two accessories 1000, 1006 can each include a motion sensor Similar to the embodiment of FIG. 16, the second accessory 1006 can be coupled to an exterior surface of the dispenser 1002.

Figure 19:
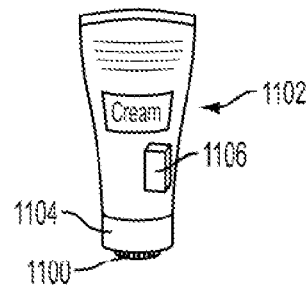
FIG. 19 is a perspective view of one embodiment of a consumables dispenser in the form of a tube of cream having first and second accessories attached thereto.

In the embodiment of FIG. 19, the accessory 1100 is coupled to a consumables dispenser 1102 in the form of a squeezable cream tube having a releasable cap 1104 at a top thereof to which the accessory 1000 is coupled. The accessory 1100 can include a pressure sensor. The dispenser 1102 in this illustrated embodiment also has a second accessory 1106 coupled thereto Similar to the embodiment of FIG. 14, the second accessory 1106 can include a motion sensor. Similar to the embodiment of FIG. 16, the second accessory 1006 can be coupled to an exterior surface of the dispenser 1102.

Figure 20:
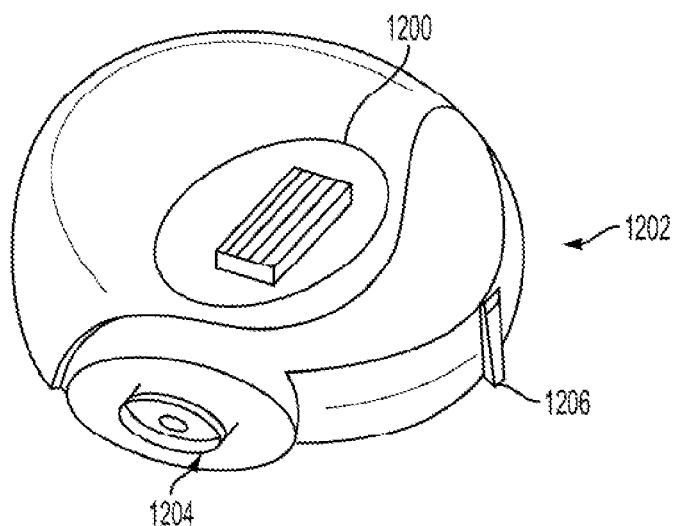
FIG. 20 is a perspective view of another embodiment of a consumables dispenser in the form of a respiratory inhaler having an accessory attached thereto.

In the embodiment of FIG. 20, the accessory 1200 is coupled to a consumables dispenser 1202 in the form of a disc-shaped respiratory inhaler having a mouthpiece 1204 through which a consumable (e.g., a dry powder) disposed in the dispenser 1202 can be dispensed in response to actuation of a slidable button 1026. Similar to the embodiment of FIG. 14, the accessory 1200 can include a motion sensor Similar to the embodiment of FIG. 16, the accessory 1200 can be coupled to an exterior surface of the dispenser 1202.

The accessory 1300 of FIG. 21 is a cap similar to the accessory 302 of FIG. 4 and is shown in FIG. 14 coupled to a top of a canister 1302 of a consumable dispenser 1304 in the form of a respiratory inhaler similar to the dispenser 304 of FIG. 4. The dispenser 1304 in this illustrated embodiment also has a second accessory 1306 coupled thereto. The second accessory 606 in this illustrated embodiment is to a bottom of the dispenser 1304 and includes a pressure sensor configured to detect pressure changes caused by movement of the canister 1302 relative to a housing 1308 of the dispenser 1304.

In some embodiments, an accessory can be configured to be attached to a bottom of a consumables dispenser. For example, the accessory can be configured to attach to a bottom of a consumables dispenser's canister adjacent a mouthpiece of the dispenser through which the consumable can be dispensed, the canister being configured to be depressed by a user to dispense the consumable out a mouthpiece of the dispenser. The accessories 1306 and 1400 of the embodiments of FIGS. 21 and 22 are examples of accessories configured to be attached to a bottom of a dispenser.

Figure 22:
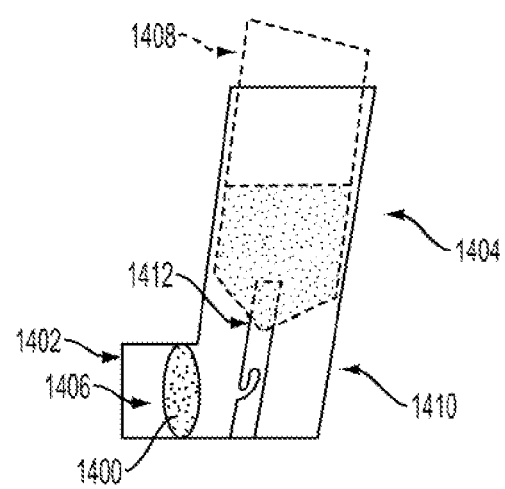
FIG. 22 is a perspective view of another embodiment of a consumables dispenser in the form of a respiratory inhaler having an accessory attached thereto.

The accessory 1400 of FIG. 22 is positioned adjacent a mouthpiece 1402 of a consumables dispenser 1404, which in this illustrated embodiment includes a respiratory inhaler, within a passageway 1406 of the dispenser's housing 1410 through which the consumable 1412 contained in the dispenser's canister 1408 can be released. The accessory 1400 in this illustrated embodiment includes an air pressure sensor configured to sense changes in air pressure In some embodiments, an accessory can be configured to be attached to a side of a consumables dispenser. For example, the accessory can be configured to attach to a sidewall of a pill bottle. For another example, the accessory can be configured to be attached to a sidewall of a dispenser housing configured to seat a medication canister therein. The accessories 606, 706, 806, 906, 1006, 1106, 1500, 1600, 1700, and 1800 of the embodiments of FIGS. 14-19, and 23-26 are examples of accessories configured to be attached to a side of a dispenser.

Figure 23:
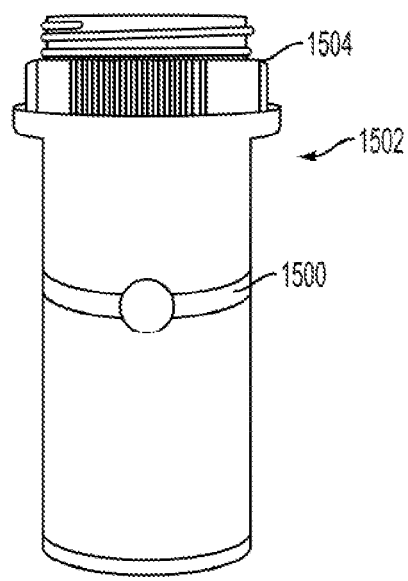
FIG. 23 is a perspective view of another embodiment of a consumables dispenser in the form of a pill bottle having an accessory attached thereto.

In the embodiment of FIG. 23, the accessory 1500 is coupled to a consumables dispenser 1502 in the form of a pill bottle similar to the dispenser 702 of FIG. 15. Similar to the embodiment of FIG. 14, the accessory 1500 can include a motion sensor and can be coupled to the dispenser 702 with a band or strap, e.g., around an exterior surface of the bottle below the bottle's cap 1504.

Figure 24:
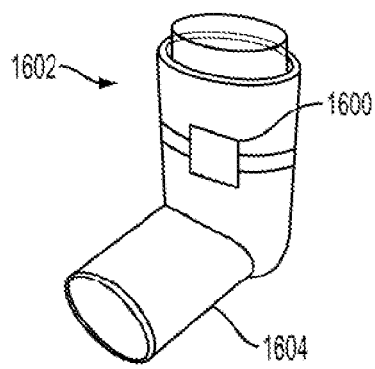
FIG. 24 is a perspective view of another embodiment of a consumables dispenser in the form of a respiratory inhaler having an accessory attached thereto.

In the embodiment of FIG. 24, the accessory 1600 is coupled to a consumables dispenser 1602 in the form of a respiratory inhaler similar to the dispenser 304 of FIG. 4. Similar to the embodiment of FIG. 14, the accessory 1600 can include a motion sensor and can be coupled to the dispenser 1602 with a band or strap, e.g., around an exterior surface of the dispenser's housing 1604.

Figure 25:
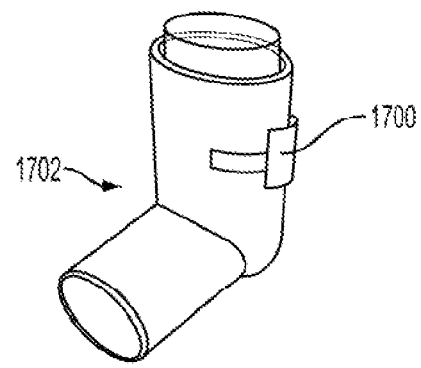
FIG. 25 is a perspective view of yet another embodiment of a consumables dispenser in the form of a respiratory inhaler having an accessory attached thereto.

In the embodiment of FIG. 25, the accessory 1700 is coupled to a consumables dispenser 1702 in the form of a respiratory inhaler similar to the dispenser 304 of FIG. 4. Similar to the embodiment of FIG. 14, the accessory 1700 can include a motion sensor and can be coupled to the dispenser 1702 with a clip, e.g., clipped to an exterior surface of the dispenser's housing 1604.

Figure 26:
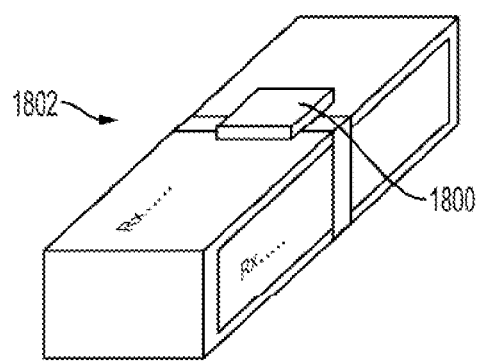
FIG. 26 is a perspective view of another embodiment of a consumables dispenser in the form of a pill box having an accessory attached thereto.

In the embodiment of FIG. 26, the accessory 1800 is coupled to a consumables dispenser 1802 in the form of a pill box similar to the dispenser 1002 of FIG. 18. The pill box 1802 in this illustrated embodiment is rectangular, while the pill box 1002 of FIG. 18 is circular. Pill boxes can have other shapes in other embodiments Similar to the embodiment of FIG. 14, the accessory 1800 can include a motion sensor and can be coupled to the dispenser 1802 with a band or strap, e.g., around an exterior surface of the dispenser 1802.

In some embodiments, an accessory can be configured to be attached to a part of a consumables dispenser configured to be manually actuated by a user to dispense the consumable from the dispenser. The part of the dispenser can be located at a variety of locations, depending on the configuration of the dispenser, e.g., at a top of the dispenser, on a side of the dispenser, etc. For example, the accessory can be configured to attach to a top of a consumables dispenser's canister, which can be configured to be depressed by a user to dispense the consumable out a mouthpiece of the dispenser. For another example, the accessory can be configured to attach to a pill bottle cap configured to be unscrewed from the pill bottle to allow consumables (e.g., pills) to be dispensed from the pill bottle. The accessory 310 of the embodiment of FIG. 4, the accessory 400 of the embodiment of FIG. 7, and accessories 600, 700, 800, 900, 1000, 1100, and 1300, of the embodiments of FIGS. 14-19 and 21 are examples of accessories configured to be attached to a part of a consumables dispenser configured to be manually actuated by a user to dispense the consumable from the dispenser.

In some embodiments, a consumables dispenser can have a plurality of accessories coupled thereto. Each of the accessories can be coupled to a top of the dispenser, each of the accessories can be coupled to a bottom of the dispenser, each of the accessories can be coupled to a side of the dispenser, each of the accessories can be coupled to a part of a consumables dispenser configured to be manually actuated by a user to dispense the consumable from the dispenser, or the accessories can each be coupled to the dispenser at different locations (e.g., one accessory coupled to a top of a dispenser and another accessory coupled to a bottom of the dispenser, one accessory coupled to a part of a consumables dispenser configured to be manually actuated by a user to dispense the consumable from the dispenser and another accessory coupled to a side of the dispenser, etc.).

FIGS. 14-19 and 21 illustrate embodiments of dispensers each having a plurality of accessories coupled thereto. A dispenser having a plurality of accessories coupled thereto can help better distinguish false positives from actual instances of the consumable being dispensed because dispensing can be verified in at least two ways, e.g., verified once with each accessory. A processor associated with the dispenser, e.g., a processor that is part of one of the accessories, can be configured to determine that a consumable was dispensed only when all of the accessories indicate that a consumable has been dispensed, e.g., when all of the accessories have been activated. A dispenser having a plurality of accessories coupled thereto can allow one of the accessories to be removed from the dispenser for repair, replacement, etc. without having to disturb the other one or more accessories coupled to the dispenser.

In an exemplary embodiment, at least one of the plurality of accessories can be removably and replaceably coupled to the dispenser, and at least one other of the plurality of accessories can be non-removably coupled to the dispenser. In this way, the dispenser can be ensured of having at least one accessory coupled thereto at all times since at least one of the accessories can be non-removably coupled thereto. Thus, if an error occurs with the removable and replaceable accessory/accessories, then dispensing of consumables can still be accurately determined by a processor associated with the dispenser considering activation of the properly attached and properly functioning one or more of the plurality of accessories. Examples of such errors include as a person forgetting to removably attach an accessory to the dispenser before using the accessory, an accessory not being properly removably coupled to the dispenser, and an accessory's battery being depleted.

In an exemplary embodiment, at least one of the plurality of accessories can be configured to be manually manipulated to cause dispensing of the consumable from the dispenser (e.g., be pressed to dispense the consumable as with an accessory in the form of a cap coupled to an inhaler canister), and at least one other of the plurality of accessories can be configured to passively detect dispensing of the consumable (e.g., be a sensor configured to passively sense a parameter such as motion, pH, temperature, noise, or geographic location). Dispensing of the consumable can thus be more accurately determined than if the dispenser has no passive accessories or if the dispenser has no accessories configured to cause consumable dispensing by user manipulation thereof because the dispensing can be detected in different ways.

A dispenser can include a plurality of accessories with at least two of the accessories including a motion-sensitive member. As discussed above, a difference in motion detected by the at least two motion-sensitive members can indicate that a consumable was dispensed. In some embodiments, each of the plurality of accessories can include a motion-sensitive member, while in other embodiments, at least two of the plurality of accessories can include a motion-sensitive member and at least one of the plurality of accessories can lack a motion-sensitive member and be configured to be detect dispensing of a consumable in another way, e.g., by sensing temperature, by being depressed, etc.

Figure 27:
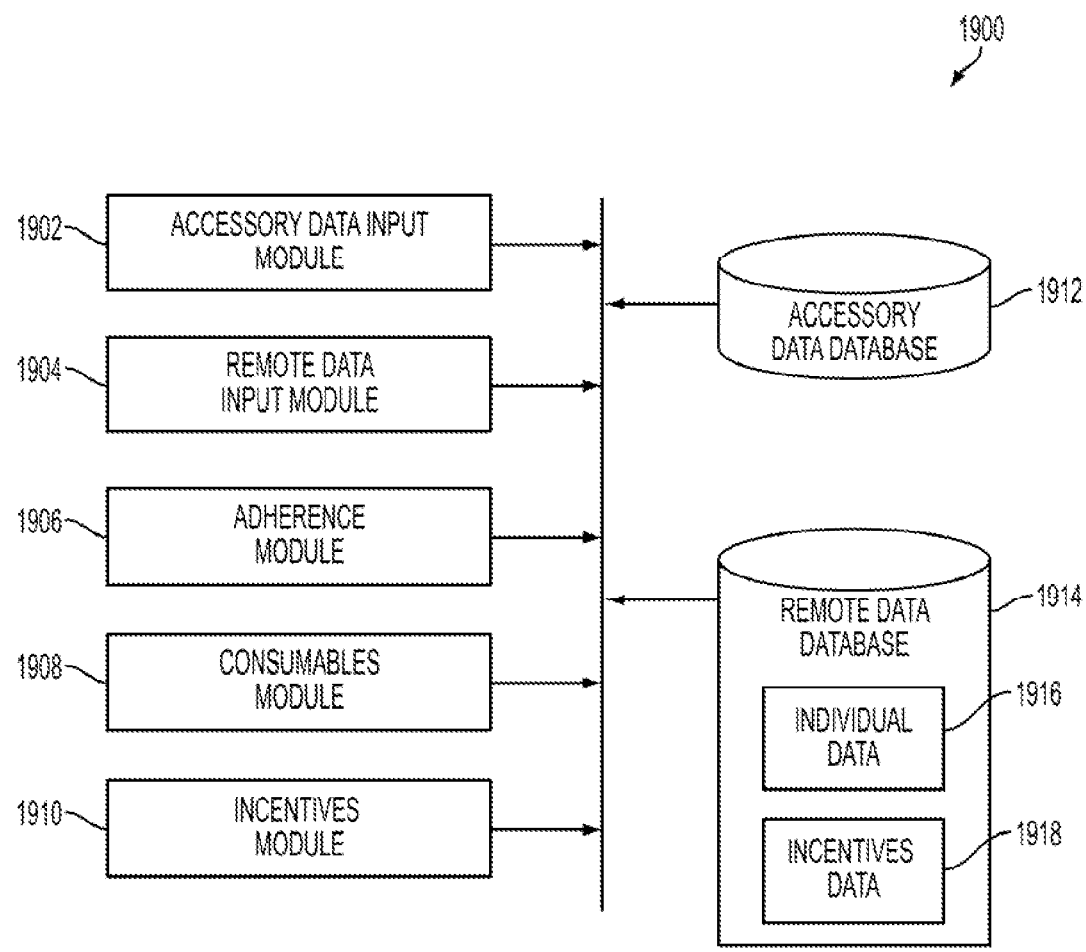
FIG. 27 is a schematic diagram of one embodiment of an adherence monitoring and patient interaction system.

FIG. 27 is a schematic block diagram of one exemplary embodiment of a consumables analysis system 1900. The system 1900 can include a plurality of modules which can each be implemented using one or more digital data processing systems of the type described above, and in particular using one or more web pages which can be viewed, manipulated, and/or interacted with using such digital data processing systems. The system 1900 can thus be implemented on a single computer system, or can be distributed across a plurality of computer systems. The system 1900 also includes at least one database, which can be stored on and accessed by computer systems. It will be appreciated by a person skilled in the art that any of the modules or databases disclosed herein can be subdivided or can be combined with other modules or databases.

The system 1900 can include an accessory data input module 1902, a remote data input module 1904, an adherence module 1906, and a consumables module 1908, and an incentives module 1910. Any of the accessory data input module 1902, the remote data input module 1904, the adherence module 1906, and the consumables module 1908, and the incentives module 1910 can be used independently from one another and can be used in combination with any one or more of the other modules 1902, 1904, 1906, 1908, 1910. Each of the modules 1902, 1904, 1906, 1908, 1910 is discussed further below in turn. Although each of the modules 1902, 1904, 1906, 1908, 1910 is illustrated in FIG. 27 as a single-component module, each of the modules 1902, 1904, 1906, 1908, 1910 can include any number of component modules, e.g., one, two, three, etc., the same or different from any of the other modules 1902, 1904, 1906, 1908, 1910. Further, as mentioned above, it will be appreciated by a person skilled in the art that any of the modules 1902, 1904, 1906, 1908, 1910, and any of their various component modules, can be subdivided or can be combined with other modules, including modules illustrated in FIG. 27 as being in different ones of the modules 1902, 1904, 1906, 1908, 1910.

The system 1900 can also include an accessory data database 1912 and a remote data database 1914. The accessory data database 1912 can be configured to be accessible by the accessory data input module 1902 and to store data regarding a mechanical accessory. The remote data database 1914 can be configured to be accessible by the remote data input module 1904 and to store data regarding individuals in an individual database 1916 and data regarding incentives in an incentives database 1918. Each of the databases 1912, 1914 can include any number of component databases, e.g., one, two, three, etc., the same or different from any of the other databases 1912, 1914. As mentioned above, a person skilled in the art will appreciate that any of the databases 1912, 1914, and any of their various component databases (if any), can be subdivided or can be combined with other databases, including databases illustrated in FIG. 27 as being in different ones of the databases 1912, 1914. Any portion of any of the databases 1912, 1914 can be configured to be accessed, e.g., read from and/or written to, by any one or more of the modules 1902, 1904, 1906, 1908, 1910 and any additional module(s) (if any). Although the system 1900 in the illustrated embodiment stores data in database(s), any of the systems disclosed herein can store data in database(s) and/or in other memor(y/ies).

Generally, the system 1900 can be configured to allow individual data 1916 to be input via the accessory data input module 1902 and remote data 1914 to be input via the remote data input module 1904. The adherence module 1906 can be configured to analyze the input individual data 1916 and/or the input remote data 1914 so as to output an indication of at least one individual's adherence to a predetermined consumables schedule. The consumables module 1908 can be configured to analyze the input individual data 1914 and/or the input remote data 1914 so as to output one or more recommended changes to a patient's predetermined consumables schedule, one or more recommended changes to how soon before a dose is due are consumable dose notifications provided to the person by an accessory attached to a consumables dispenser, and/or one or more recommended changes to a patient's consumable (e.g., change to different brand, etc.). The incentives module 1910 can be configured to analyze the input individual data 1916 and/or the input remote data 1914 so as to output incentives data for at least one individual. The system 1900, embodiments thereof, and embodiments of user interfaces that can be provided thereby are described in further detail in previously mentioned Intl. App. No. PCT/US13/047507.

Although the invention has been described by reference to specific embodiments, a person skilled in the art will understand that numerous changes may be made within the spirit and scope of the inventive concepts described. A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An apparatus for attachment to an inhalation device, the apparatus comprising:
    a memory;
    a processor;
    a sensor configured to sense when the apparatus is attached to the inhalation device and cause the processor to store data in the memory regarding a sensed attachment, the apparatus being removably and replaceably attachable to the inhalation device; and
    a wireless communication mechanism; and
    wherein the processor is configured to cause the wireless communication mechanism to wirelessly transmit the data in the memory regarding the sensed attachment to an external device that is external to the apparatus and the inhalation device.

2. The apparatus of claim 1, wherein the sensor is further configured to sense when the apparatus is removed from the inhalation device, and the processor is further configured to receive a signal from the sensor in response to the sensor sensing the apparatus being removed from the inhalation device.

3. The apparatus of claim 1, wherein the sensor includes at least one of a motion sensor or a pressure sensor, and the sensor is further configured to sense when a consumable is dispensed from the inhalation device.

4. The apparatus of claim 1, wherein the sensor includes a pressure sensor, the pressure sensor being configured to have pressure applied thereto by the inhalation device in response to the apparatus being attached to the inhalation device, and the processor is further configured to determine that the apparatus has been attached to the inhalation device when the pressure sensor has the pressure applied thereto.

5. The apparatus of claim 4, wherein the pressure sensor is configured to have the pressure released therefrom in response to the apparatus being removed from the inhalation device, and the processor is further configured to determine that the apparatus has been removed from the inhalation device when the pressure sensor has the pressure released therefrom.

6. The apparatus of claim 1, wherein the sensor includes a motion sensor, and the processor is further configured to determine that the apparatus has been attached to the inhalation device when the motion sensor senses a first predetermined motion of the apparatus.

7. The apparatus of claim 6, wherein the processor is further configured to determine that the apparatus has been removed from the inhalation device when the motion sensor senses a second predetermined motion of the apparatus that is different from the first predetermined motion.

8. The apparatus of claim 1, wherein the sensor is further configured to sense when an electrical circuit is closed, thereby indicating that the apparatus has been attached to the inhalation device.

9. The apparatus of claim 1, wherein the sensor is a first sensor, and the apparatus further comprises a second sensor configured to sense when a consumable is dispensed from the inhalation device.

10. The apparatus of claim 9, wherein the apparatus includes the first sensor at a first location and includes the second sensor at a second location that is different from the first location.

11. An apparatus for attachment to an inhalation device, the apparatus comprising:
    a memory;
    a processor;
    a sensor configured to sense attachment of the apparatus to the inhalation device using one or more of pressure sensing or motion sensing, and to cause the processor to store data in the memory regarding a sensed attachment, wherein the apparatus is removably and replaceably attachable to the inhalation device; and
    a wireless communication mechanism; and
    wherein the processor is configured to:
        cause the apparatus to provide a first notification in response to the sensor sensing that the apparatus is attached to the inhalation device so as to notify a user that the apparatus has been attached to the inhalation device;
        cause the wireless communication mechanism to wirelessly transmit the data in the memory regarding the sensed attachment to an external device that is external to the apparatus and the inhalation device; and
        determine when a consumable is dispensed from the inhalation device.

12. The apparatus of claim 11, wherein the sensor comprises at least one of a motion sensor or a pressure sensor, and the sensor is further configured to sense when the consumable is dispensed from the inhalation device.

13. The apparatus of claim 11, wherein the sensor is further configured to sense when the apparatus is removed from the inhalation device, and the processor is further configured to provide a second notification when the sensor senses that the apparatus is removed from the inhalation device so as to notify the user that the apparatus has been removed from the inhalation device.

14. The apparatus of claim 11, wherein the sensor is a first sensor, and the apparatus further comprises a second sensor configured to sense when the consumable is dispensed from the inhalation device.

15. The apparatus of claim 11, wherein the inhalation device comprises a housing having the consumable disposed therein, the apparatus being removably and replaceably attachable to an external surface of the housing.

16. A method comprising:
    sensing, via a sensor, an attachment of an apparatus to an inhalation device;
    storing a first data in a memory regarding a sensed attachment;
    wirelessly transmitting, via a transmitter, the first data in the memory regarding the sensed attachment to an external device, the external device being external to the apparatus and the inhalation device; and
    wirelessly transmitting, via the transmitter, a second data from the apparatus to the external device, the second data being indicative of a dispensing of a consumable contained in the inhalation device.

17. The method of claim 16, further comprising:
sensing, via the sensor, detachment of the apparatus from the inhalation device; and
wirelessly transmitting, via the transmitter, a third data from the apparatus to the external device, the third data being indicative of a sensed detachment.

18. The method of claim 16, further comprising:
providing a notification to a user indicating that the consumable is due to be consumed according to a predetermined schedule.

* * * * *